United States Patent
Farbood et al.

(10) Patent No.: US 6,271,194 B1
(45) Date of Patent: Aug. 7, 2001

(54) OPTICAL ISOMER OF DELTA DECALACTONE AND ORGANOLEPTIC USES THEREOF

(75) Inventors: Mohamad I. Farbood, State College, PA (US); Laura E. Kizer, Highlnds, NJ (US); James A. Morris, Freehold, NJ (US); Gail Harris; Lynda B. McLean, both of Matawan, NJ (US); Robert W. Blocker, Brick, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 09/468,592

(22) Filed: Dec. 21, 1999

Related U.S. Application Data

(63) Continuation-in-part of application No. 09/064,742, filed on Apr. 23, 1998, now Pat. No. 6,117,835.

(51) Int. Cl.[7] .............................. A61K 7/46; C07D 319/00
(52) U.S. Cl. .................... 512/11; 549/274; 426/3
(58) Field of Search ............................ 512/11; 549/274; 426/3

(56) References Cited

U.S. PATENT DOCUMENTS

| | | |
|---|---|---|
| 4,532,364 | 7/1985 | Fujioka et al. . |
| 4,582,635 | 4/1986 | Furuuchi et al. . |
| 4,609,492 | 9/1986 | Hata et al. . |
| 4,629,586 | 12/1986 | Wilson et al. . |
| 4,650,604 | 3/1987 | Broekhof et al. . |
| 4,709,707 | 12/1987 | Pittet et al. . |
| 4,794,193 | 12/1988 | Pittet et al. . |
| 5,525,589 | 6/1996 | Etzweiler et al. . |
| 5,739,100 | 4/1998 | Horino et al. . |
| 5,874,398 | 2/1999 | Surburg et al. . |
| 6,117,835 | * 9/2000 | Farbood et al. ..................... 512/11 |

* cited by examiner

*Primary Examiner*—Jill Warden
*Assistant Examiner*—Monique T. Cole
(74) *Attorney, Agent, or Firm*—Joseph F. Leightner

(57) ABSTRACT

Described are optical isomers of (+) δ-decalactone and (+) δ-dodecalactone which impart, augment and/or enhance the aroma and/or taste of consumable materials including foodstuffs, chewing gums, toothpastes, beverages, fragrance compositions, colognes and perfumed articles such as solid or liquid anionic, cationic, nonionic or zwitterionic detergents, fabric softeners and hair preparations. The optical isomers are produced by means of a two-phase, environmentally friendly fermentation process for producing high yields of (+) δ-decalactone and (+) δ-dodecalactone from the corresponding unsaturated starting materials. The (+) δ-decalactone substantially has the structure:

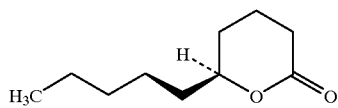

with a very minor amount of isomer having the structure:

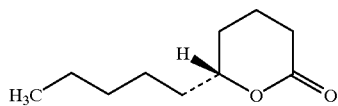

and an optical rotation of +53.64° ( $(\alpha_D^{20}=+53\cdot 64°)$ ). The (+) δ-decalactone, which is the subject of the invention, has an enantiomeric excess percent of 95.6 ([εε%=95.6]).

6 Claims, 16 Drawing Sheets

GLC. PROFILE FOR EXAMPLE I .

GLC. PROFILE FOR EXAMPLE I.

GLC PROFILE FOR EXAMPLE II.

GLC PROFILE FOR EXAMPLE III.

GLC PROFILE FOR EXAMPLE IV.

GLC PROFILE FOR EXAMPLE V.

GLC PROFILE FOR EXAMPLE VI.

FIG. 7 GC-MS PROFILE FOR EXAMPLE I.

GC - MS PROFILE

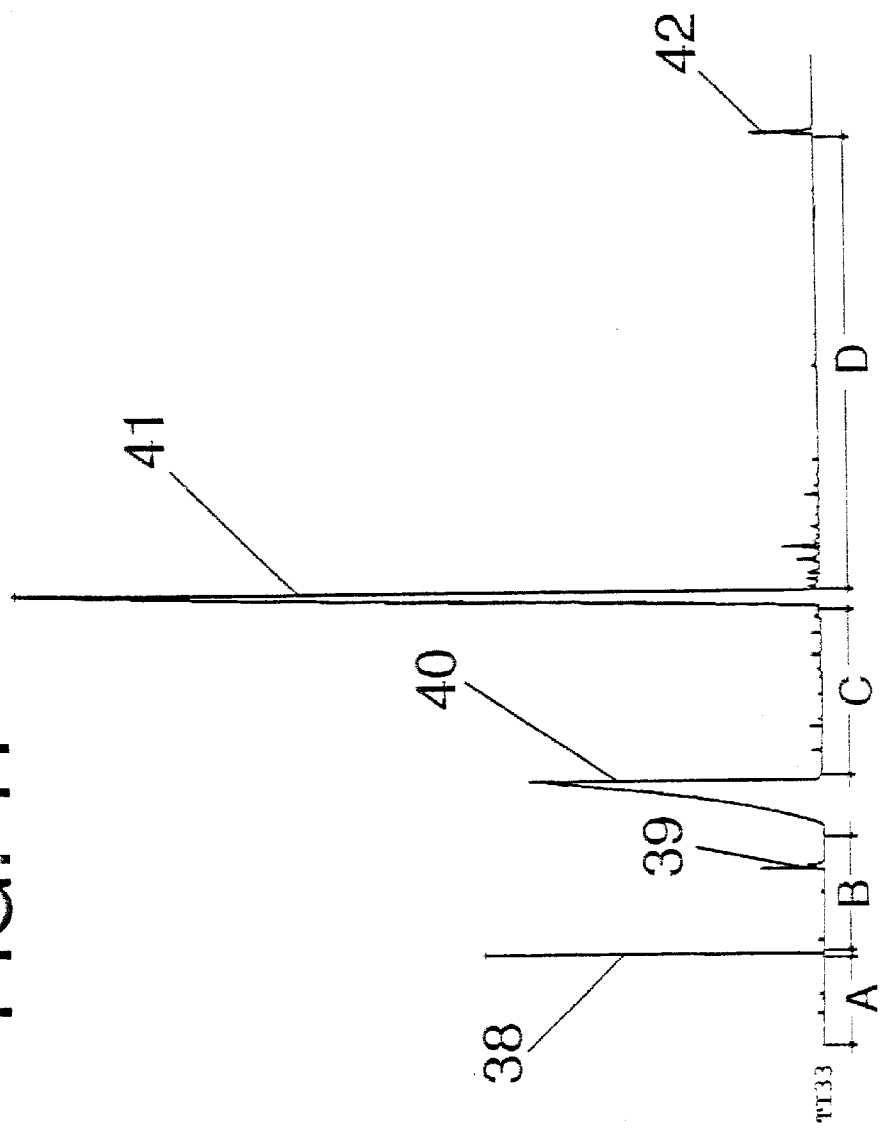

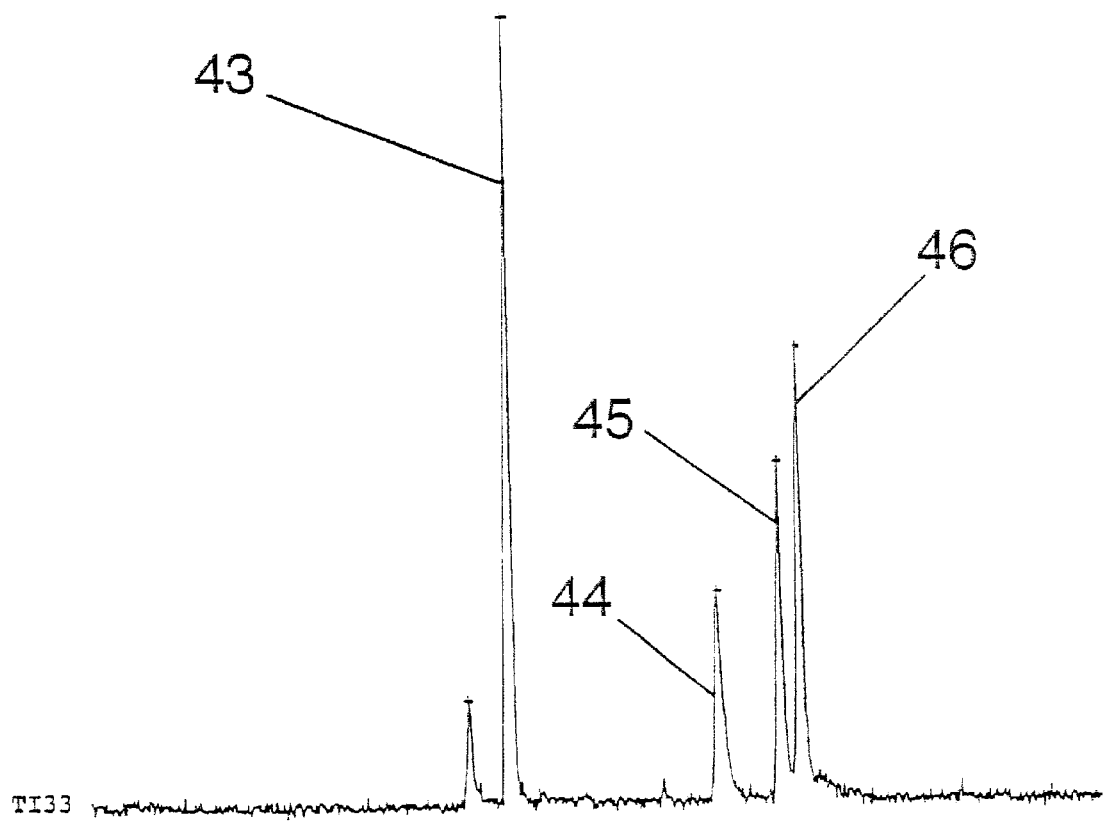
FIG. 11-A

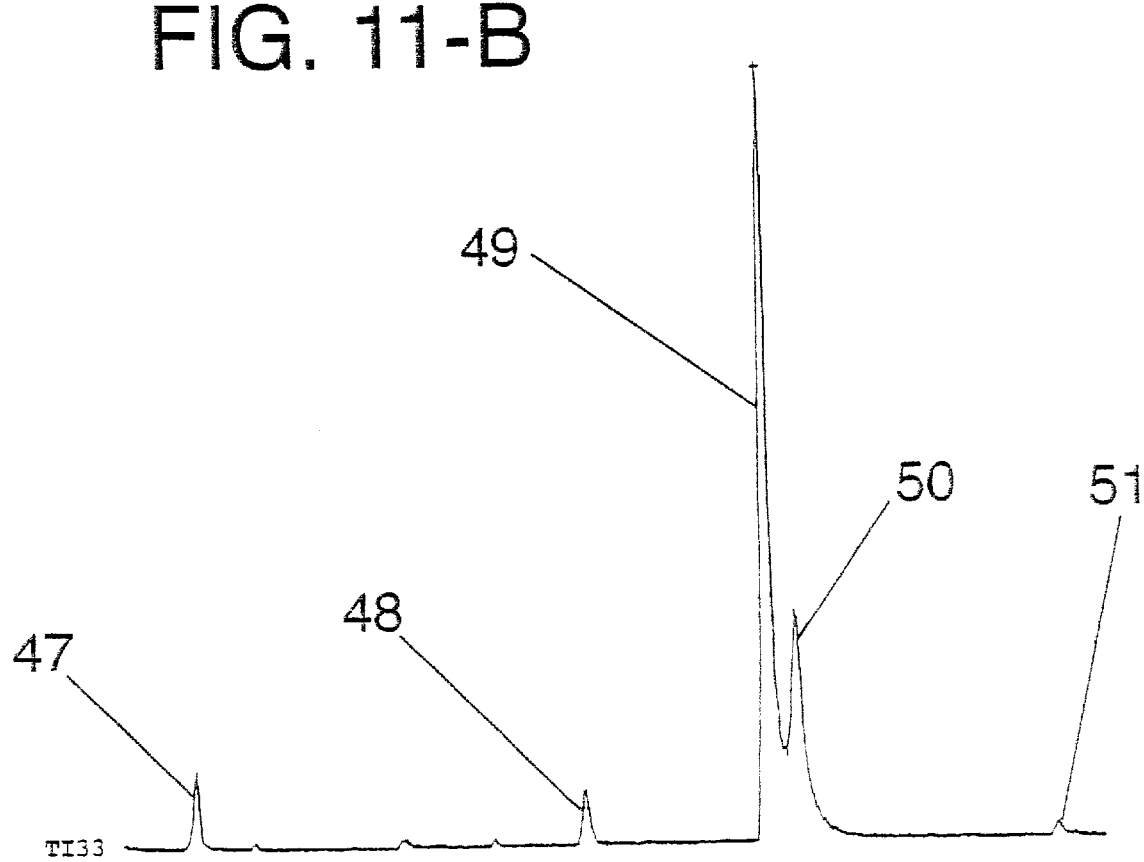
FIG. 11-B

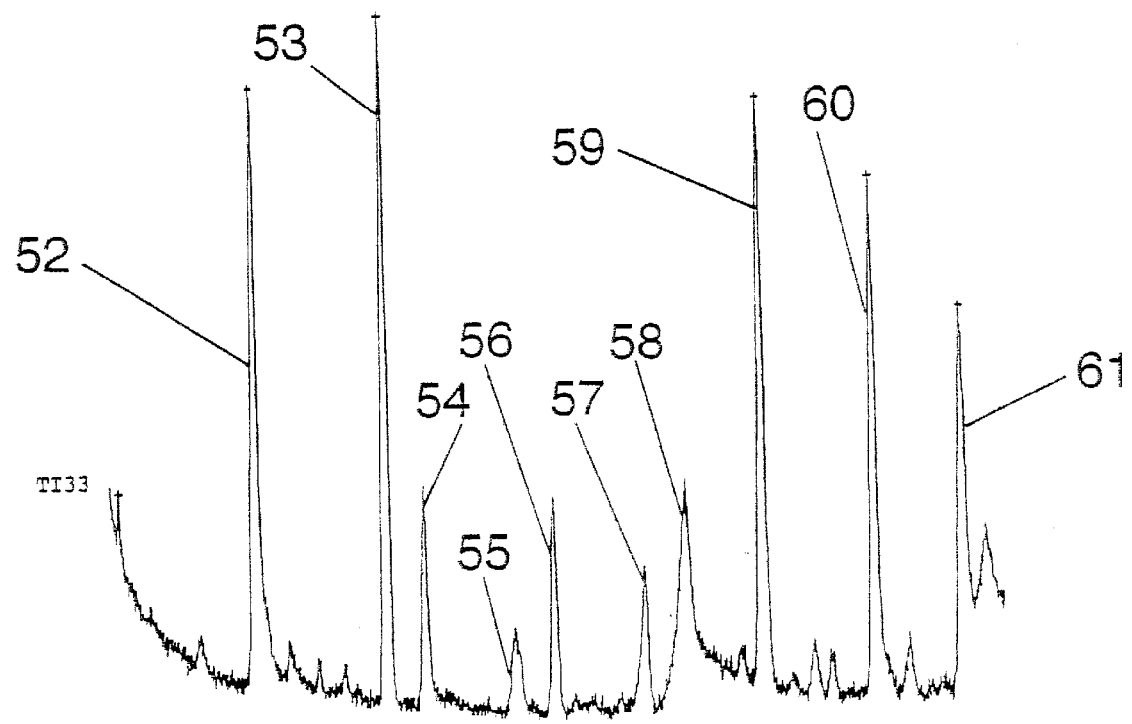
FIG. 11-C

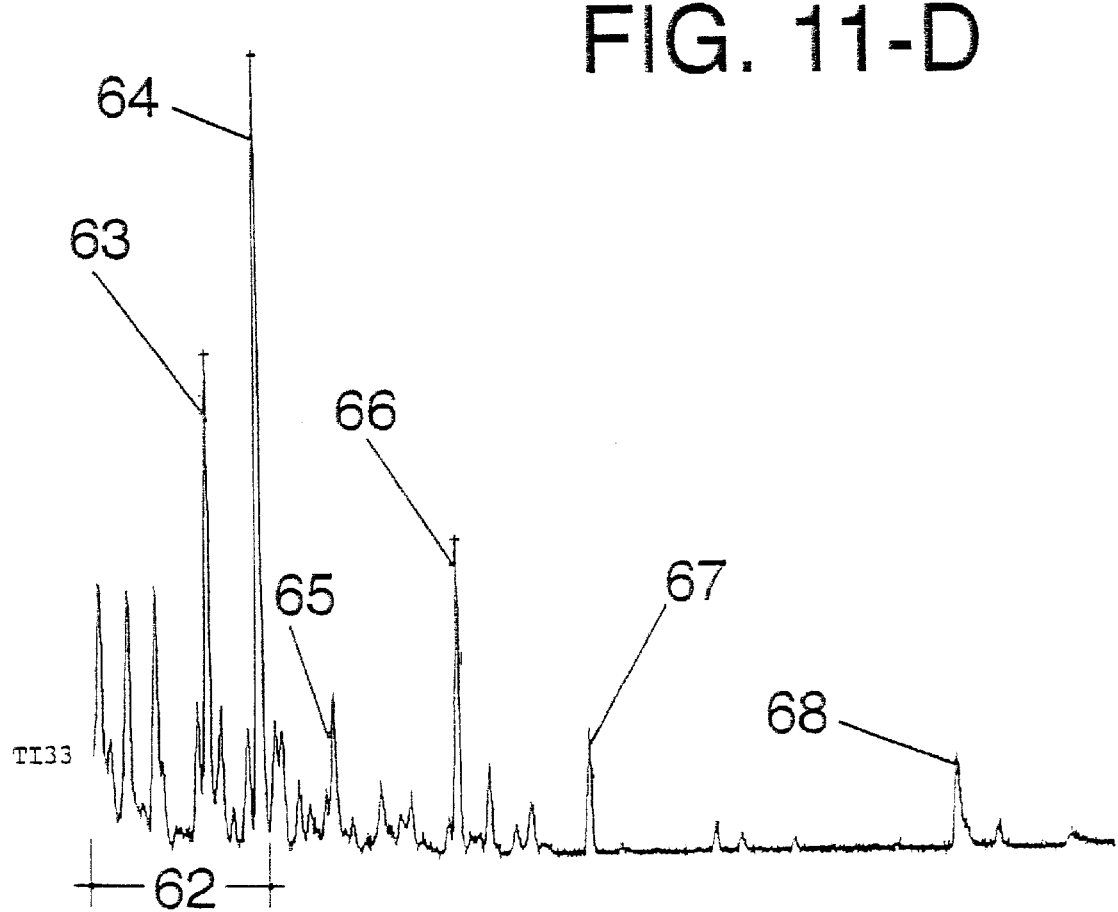

OPTICAL ISOMER OF DELTA DECALACTONE AND ORGANOLEPTIC USES THEREOF

RELATED APPLICATIONS

This application is a Continuation-in-Part of copending application for United States Leetters Patent, Ser. No. 09/064,742 filed on Apr. 23, 1998 now U.S. Pat. No. 6,117,835.

BACKGROUND OF THE INVENTION

The present invention relates to a Δ-decalatone isomer produced by means of a two phase microbial process. In a further aspect, the present invention relates to organoleptic uses of said Δ-decalactone optical isomer.

In today's market, it is frequently desirable to identify flavor components of food items as being "natural flavors." It is generally recognized in the industry that a flavor compound having been prepared by microbial processes can be designated as a natural product and therefore have an important place in the commercialization of products containing them. As a result, the industry has devoted considerable time and effort to develop methods for the production of flavoring components and, in particular, for the production of lactones which can be called "natural."

Thus, as an example of such prior developments, a method for preparing certain optically active Δ-lactones and the corresponding hydroxycarboxylic acids by microbial reduction of ketocarboxylic acids is shown in U.S. Pat. No. 3,076,750.

Investigations reported in the *Journal of Biochemistry*, 54, pages 536–540 (1963) relate to metabolism of ricinoleic acid by some Candida strains and show that γ-hydroxydecanoic acid is an intermediate in the oxidative degradation of ricinoleic acid. In a number of such prior disclosed methods, the processes were not entirely satisfactory because of the toxicity of certain components to the microorganism.

A method of producing optically active γ-hydroxydecanoic acid by culturing or incubating a microorganism capable of hydrolyzing caster oil and effecting β-oxidation of the resulting hydrolysate in the presence of caster oil to produce γ-hydroxydecanoic acid is shown in U.S. Pat. No. 4,560,656.

This reference also discloses a method of producing optically active γ-hydroxydecanoic acid by enzymatically hydrolyzing castor oil using lipase to form an enzymatic hydrolyzate and culturing a microorganism capable of effective β-oxidation of the enzymatic hydrolyzate in the presence of the hydrolyzate to produce γ-hydroxydecanoic acid. Similarly, a way of culturing or incubating the microorganism capable of hydrolyzing castor oil and a microorganism capable of affecting β-oxidation of the castor oil hydrolyzate in the presence of the castor oil to produce γ-hydroxydecanoic acid is also shown in that document.

European Published Patent Application No. 258993 of Apr. 9, 1988 discloses a process for the production of optically active γ-hydroxydecanoic acid suitable for conversion to optically active Δ-decalatone.

Microbial production of natural δ-dodecalactone from Massoi bark oil was discussed by van der Shaft, et al in *Applied Microbiology and Biotechnology* (1992), Volume 36, pages 712–716.

The usefulness of yeast for reduction reactions in general, including conversion of Massoi lactone is referred to by N. J. Turner in *Chemistry & Industry*, Aug. 1, 1994, pages 592, et seq.

Japanese Application No. 09 031071-A discloses production of (R)-(−) Massoi lactone by incubating a microorganism.

More recently, in U.S. Pat. No. 5,128,261, 5-decanolide and 5-dodecanolide have been shown to be produced from a series of strains of yeast in a fermentation reaction by carrying out a biocatalytic reduction of the corresponding natural unsaturated 5-olides.

Such prior methods are said to be economically attractive, but there is a constant need for improvement of yields and conversion which is addressed in this invention.

In the flavor and fragrance art the need has arisen for the development of more efficient production of naturally occurring lactones which have heretofore been found to be useful and necessary in the creation of flavor formulation used in augmenting or enhancing the aroma or taste of such items as foodstuffs, chewing gums and toothpastes, and also useful in augmenting or enhancing the aroma of perfume compositions such as colognes, perfumed articles, either in solid or liquid state, as for example, ionic, cationic, nonionic or zwitterionic detergents, perfumed polymers, fabric softener compositions, fabric softener articles, hair preparations, cosmetic powders and the like.

It is therefore an object of the present invention to provide a natural optical isomer of Δ-decalatone produced by means of a new and improved method.

SUMMARY OF THE INVENTION

The above and other objects and features of the invention are obtained in accordance in the present invention by carrying out a process using oxidative reaction techniques to produce and recover certain naturally occurring saturated lactones found to be useful for their organoleptic properties in augmenting or enhancing the aroma or taste of consumable materials such as foodstuffs, chewing guns, toothpastes, additional products, chewing tobaccos, smoking tobaccos, perfume compositions, colognes and perfumed articles such as solid or liquid detergents, perfumed polymers, fabric softener compositions, fabric softener articles, cosmetic powders, hair preparations and the like, which saturated lactones are optical isomers having substantially the structure:

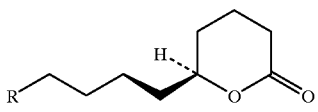

(and containing a very minor amount of isomers having the structure:

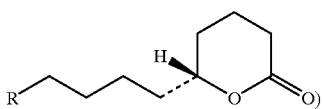

wherein R is a member selected from the group consisting of methyl and n-propyl. These compounds are primarily (+) δ-decalactone and (+) δ-dodecalactone, respectively. The optical rotation of the Δ-decalatone optical isomer mixture, substantially containing the optical isomer having the structure:

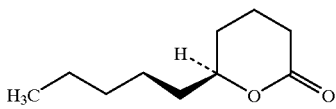

with a very minor amount of optical isomer having the structure:

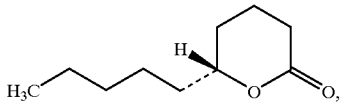

having an enantiomeric excess % of 95.6 [εε%=95.6] is +53.64° ($\alpha_D^{20}$=+53·64°).

The process to produce the lactone compositions of the invention are carried out under oxidative growth conditions by preparing (1) an aqueous nutrient medium including a source of sugar in a first aqueous liquid phase; and (2) a second nonaqueous, organic liquid phase (which is the "organic" phase) containing a significant concentration of the unsaturated 5-olide compound represented by the structural formula:

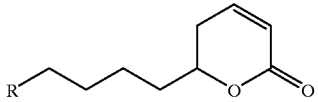

II wherein R is a member selected from a group consisting of methyl and n-propyl. The starting materials thus can be a natural 2-decen-1,5-olide or a natural 2-dodecen-1,5-olide compound.

The first aqueous liquid phase and the second organic liquid phase are mixed together with agitation to form a two-phase system while (i) maintaining sufficiently low dextrose levels and (ii) aerating with an oxygen-containing gas such as air or oxygen, whereby oxidative growth is achieved with surprisingly high conversion of the unsaturated 5-olide compound into the corresponding saturated 5-olide compound. The reaction is carried out in the presence of a selected yeast capable of producing the natural δ-lactone.

A further feature of the present invention resides in the products produced by the present invention characterized by the GLC profiles which accompany this application.

Still further, another feature of the invention resides in the flavor and fragrance compositions containing the δ-decalatone and δ-dodecalactone products produced by the present invention.

BRIEF DESCRIPTION OF THE DRAWINGS

The present invention will be further understood with reference to the accompanying drawings wherein.

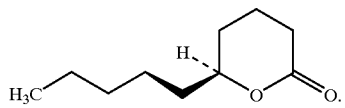

Figure 3:
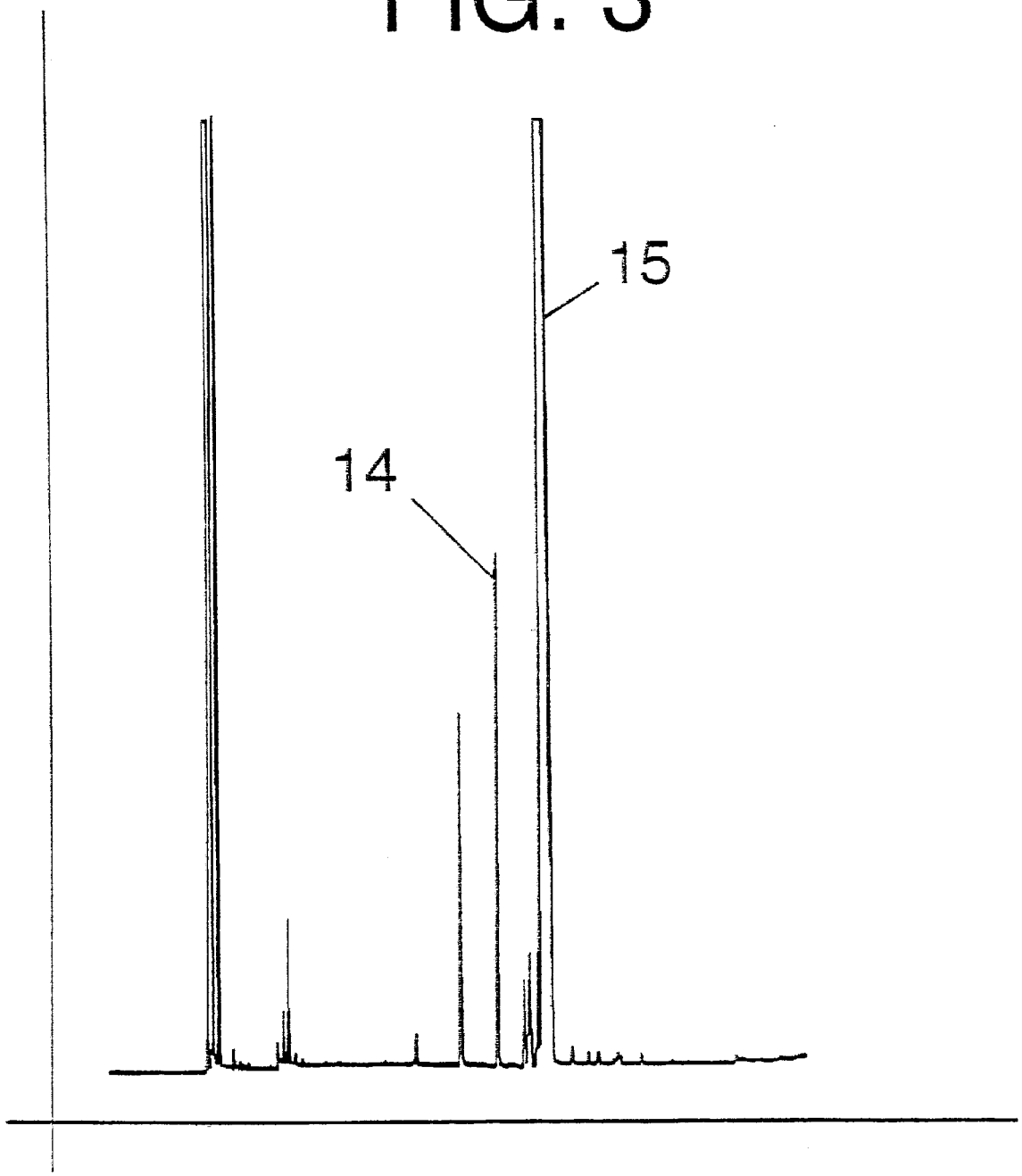

FIG. 3 is a GLC profile for the reaction product of Example III containing the compound having the structure:

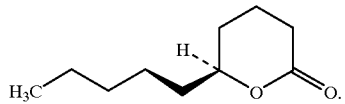

Figure 4:
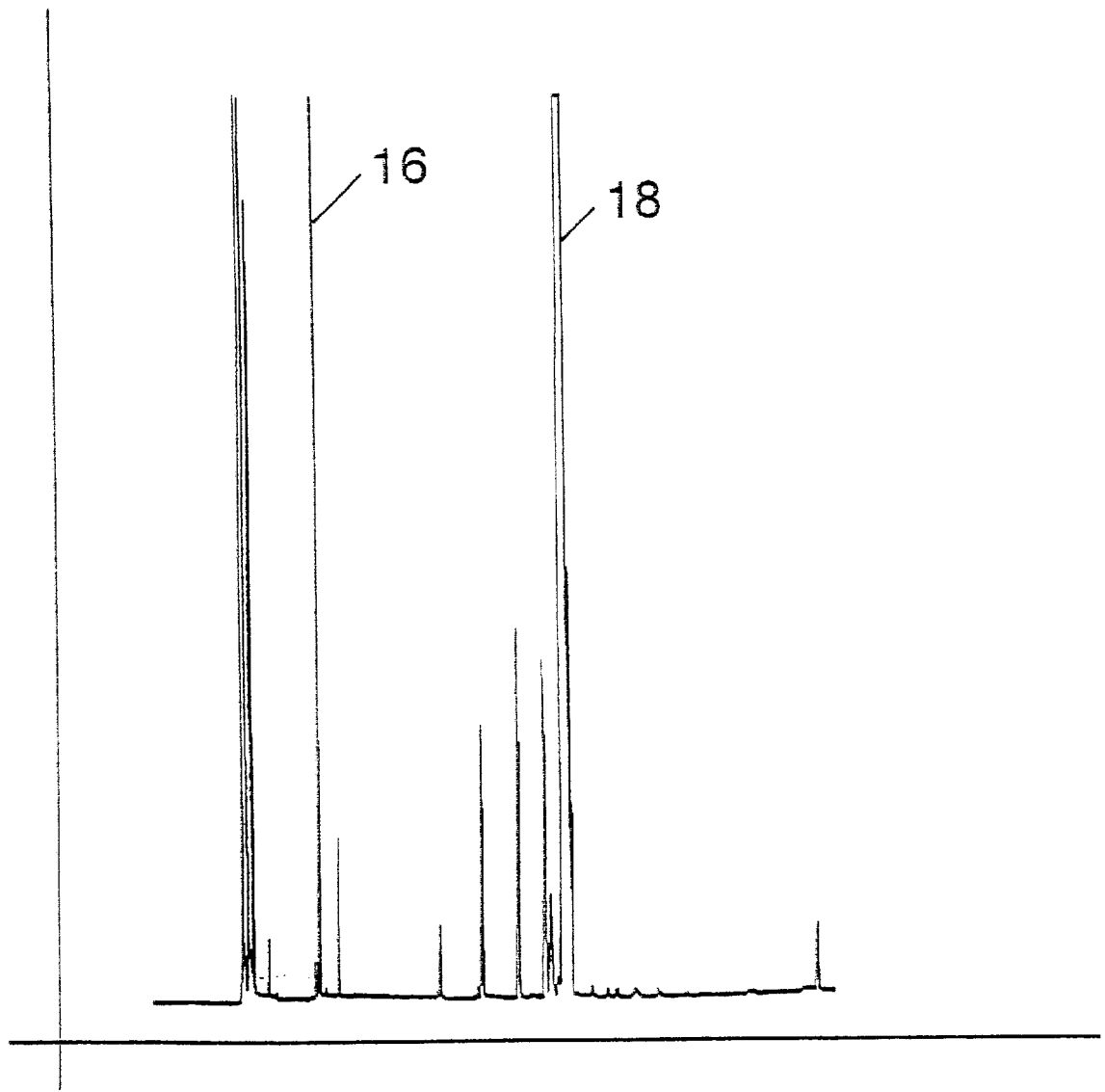

FIG. 4 is a GLC profile of the reaction product of Example IV containing the compound having the structure:

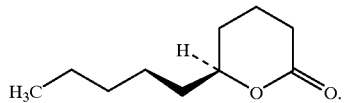

Figure 5:
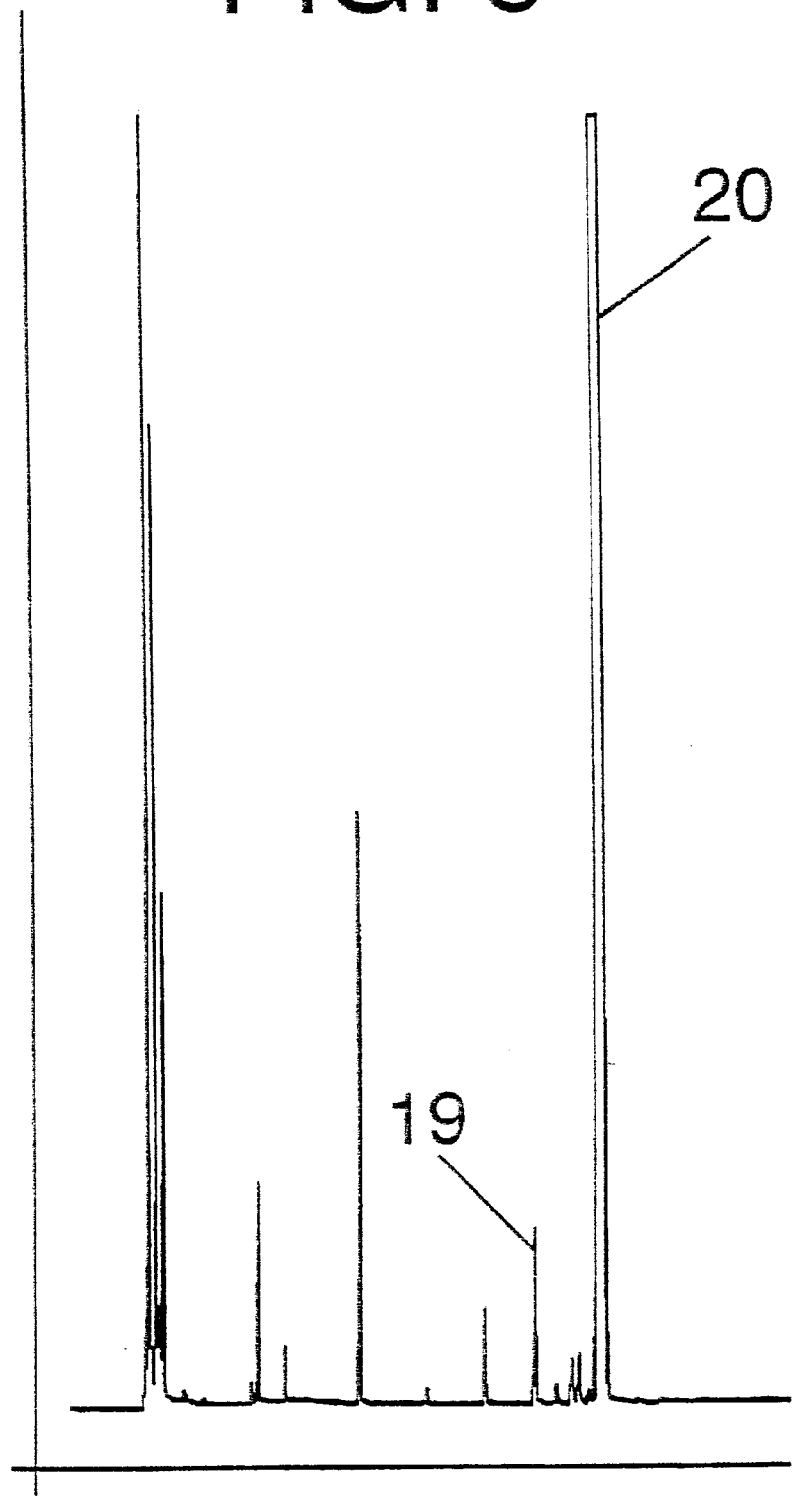

FIG. 5 is a GLC profile for the reaction product of Example V containing the compound having the structure:

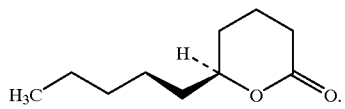

Figure 6:
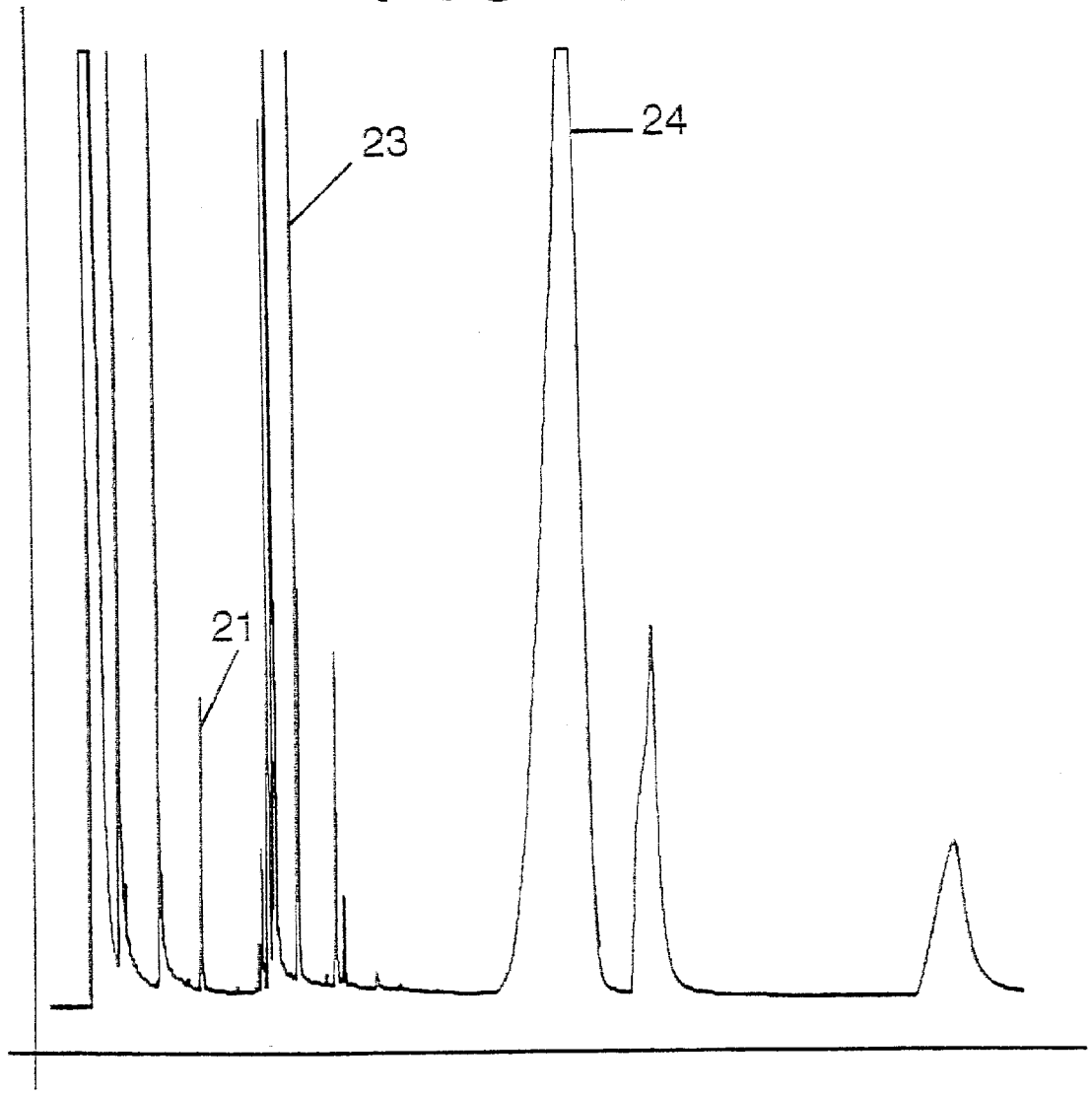

FIG. 6 is a GLC profile for the reaction product of Example VI containing the compound having the structure:

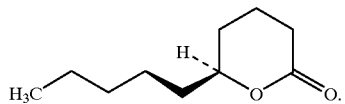

Figure 7:
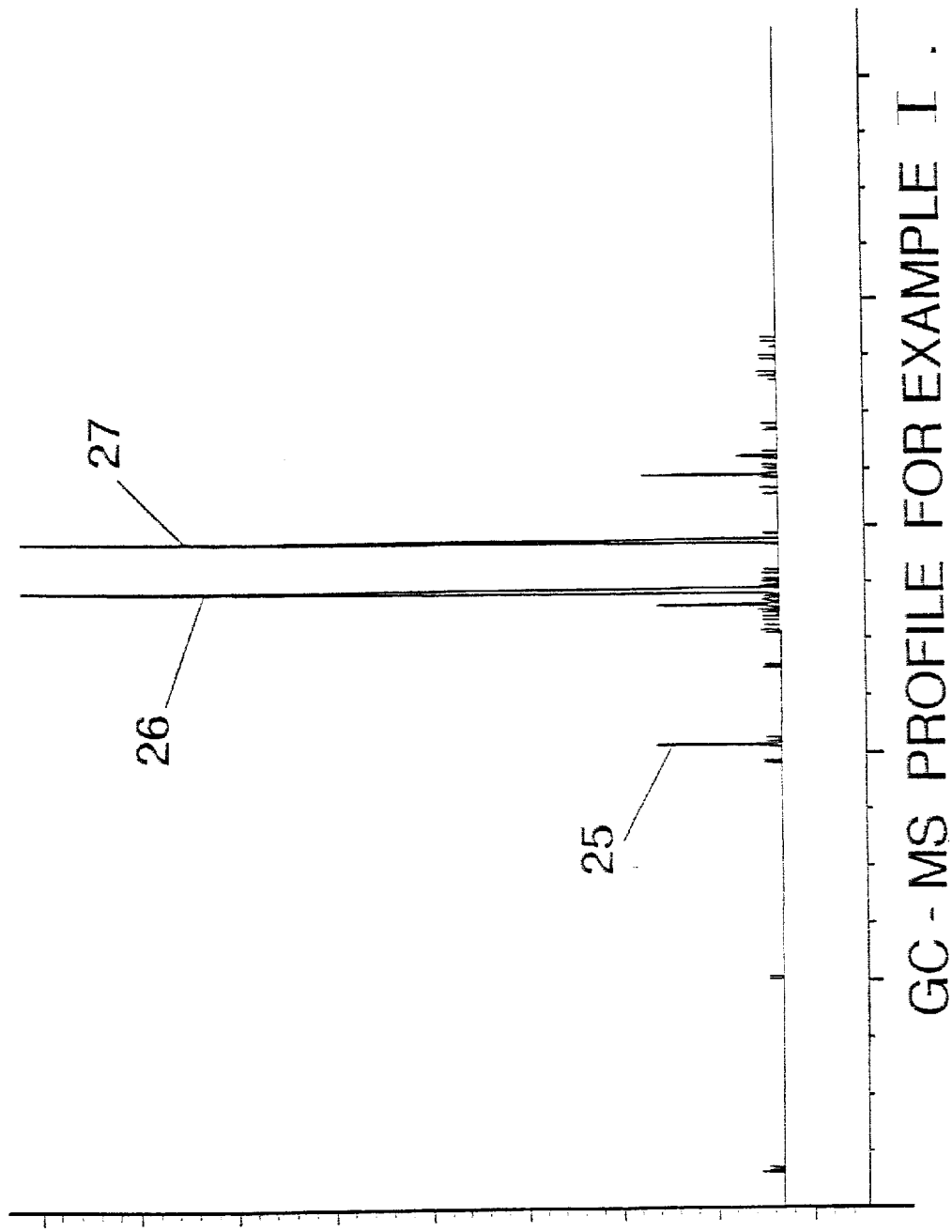

FIG. 7 is a mass spectrum for the starting material Massoi bark oil used as a starting material in Example I.

Figure 8:
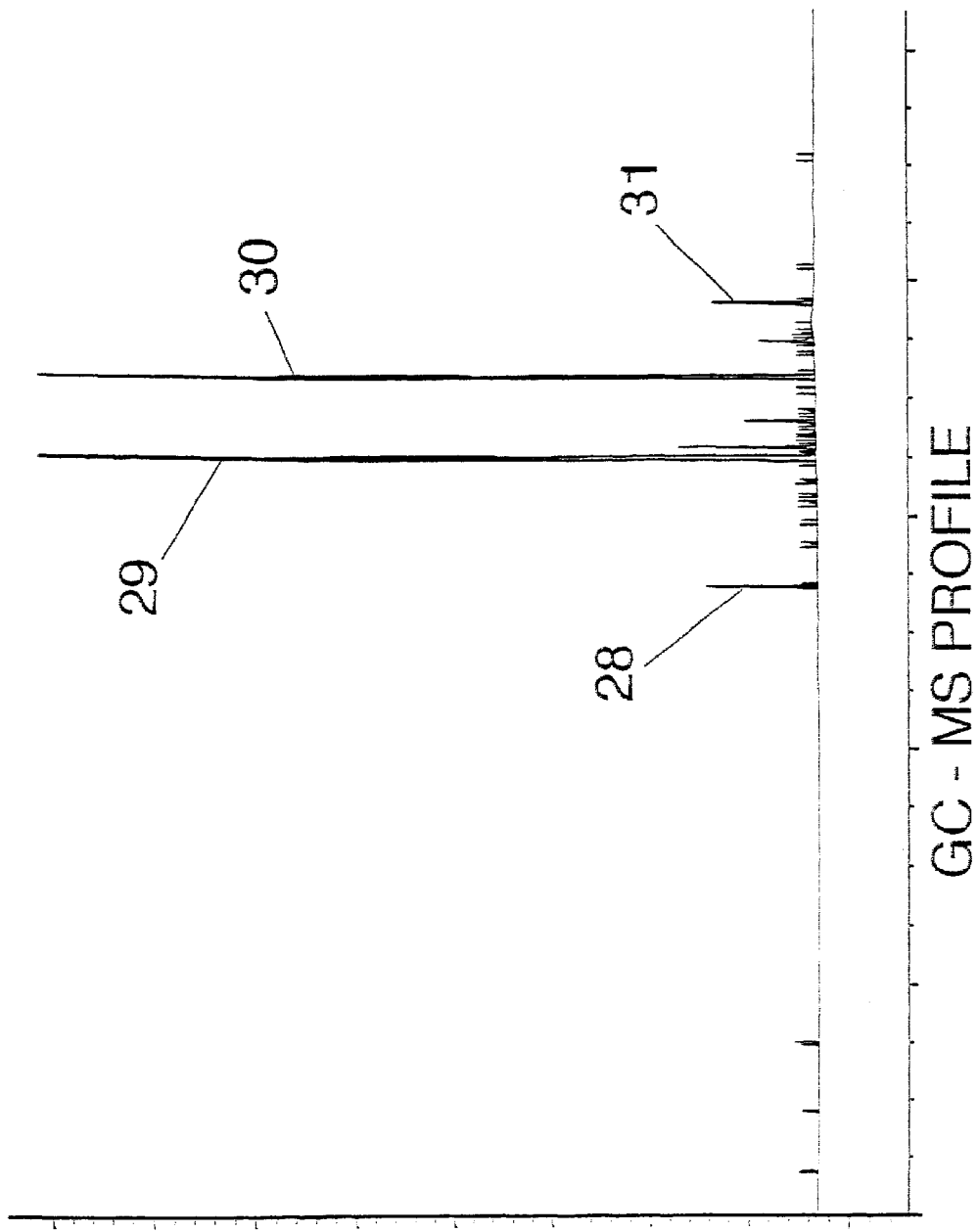

FIG. 8 is a mass spectrum for the starting material Massoi bark oil used as a starting material according to the invention.

Figure 9:
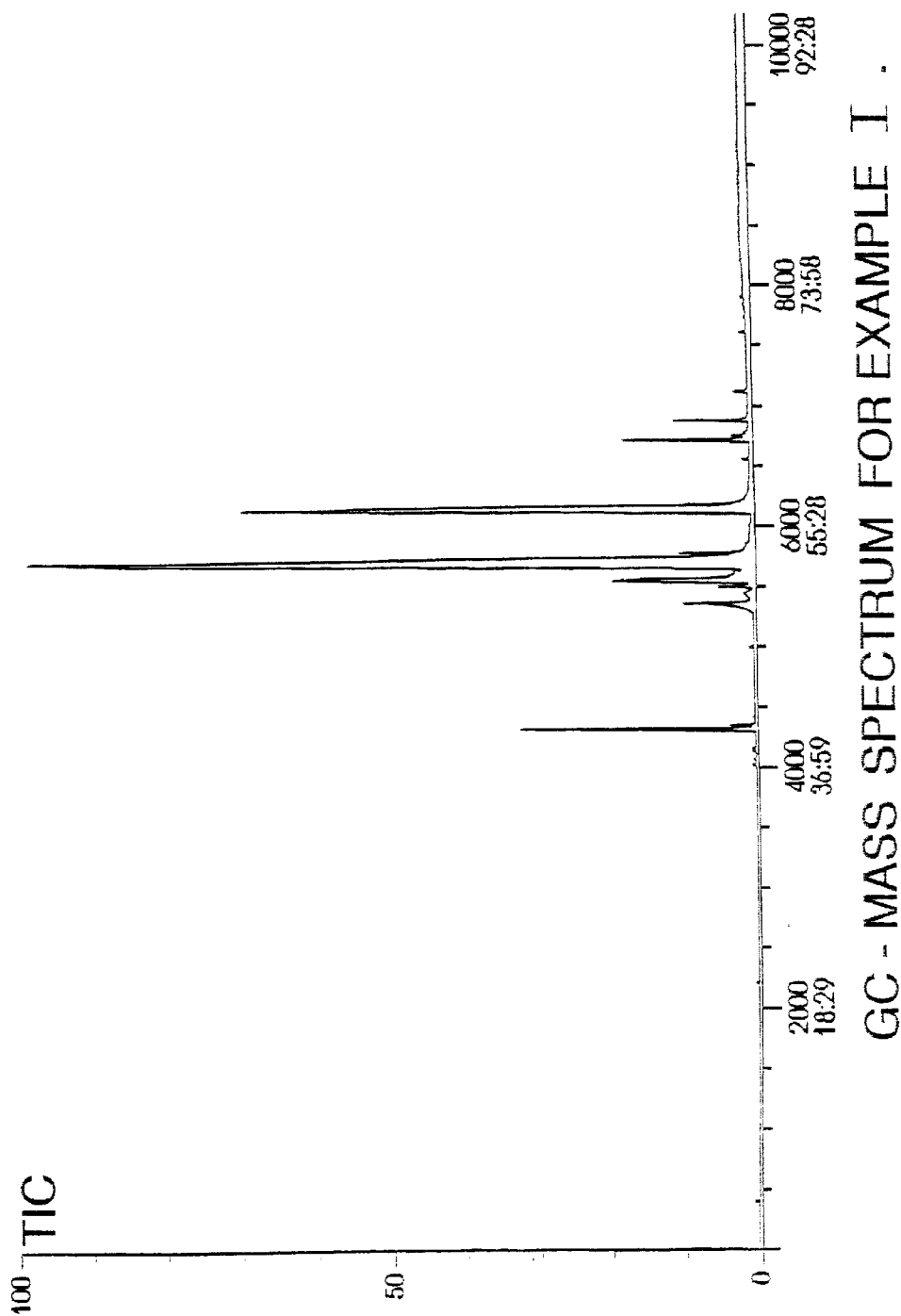

FIG. 9 is a mass spectrum for the starting material used in Example I.

Figure 10:
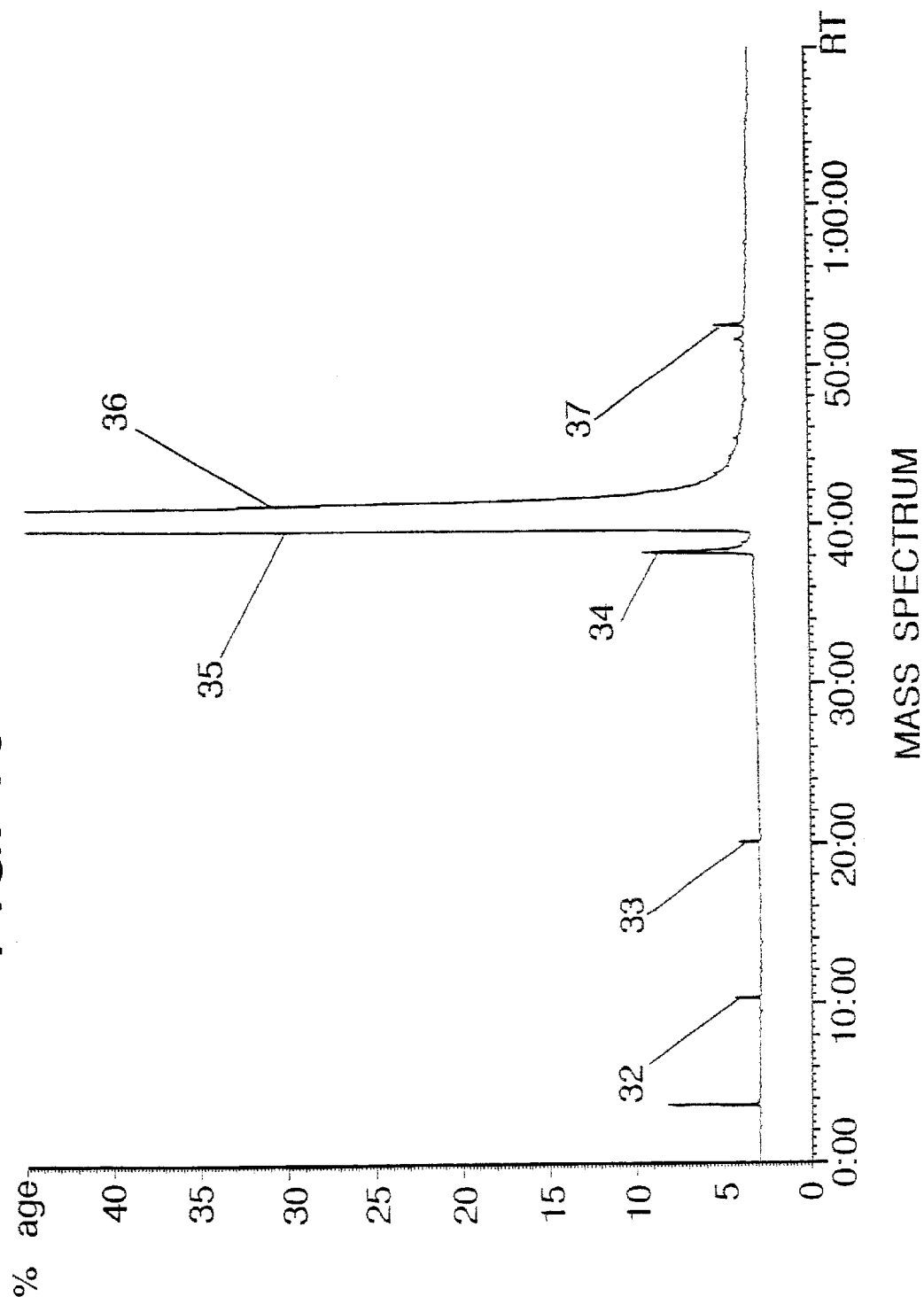

FIG. 10 is a mass spectrum of the starting material which contains 0.93% of a mixture of lactones having the structures:

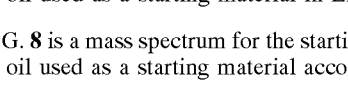
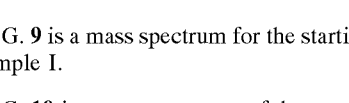

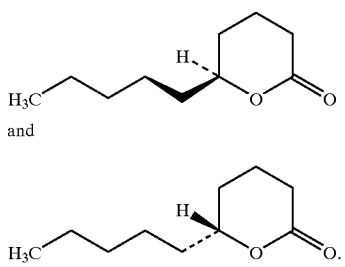

and

FIG. 11 is a mass spectrum total ion chromatogram (TIC) of the distillation fraction 2 of Example I.

FIG. 11A is an expanded TIC of section A shown in FIG. 11.

FIG. 11B is an expanded TIC of section B shown in FIG. 11.

FIG. 11C is an expanded TIC of section C shown in FIG. 11.

FIG. 11D is an expanded TIC of section D shown in FIG. 11.

Figure 12:
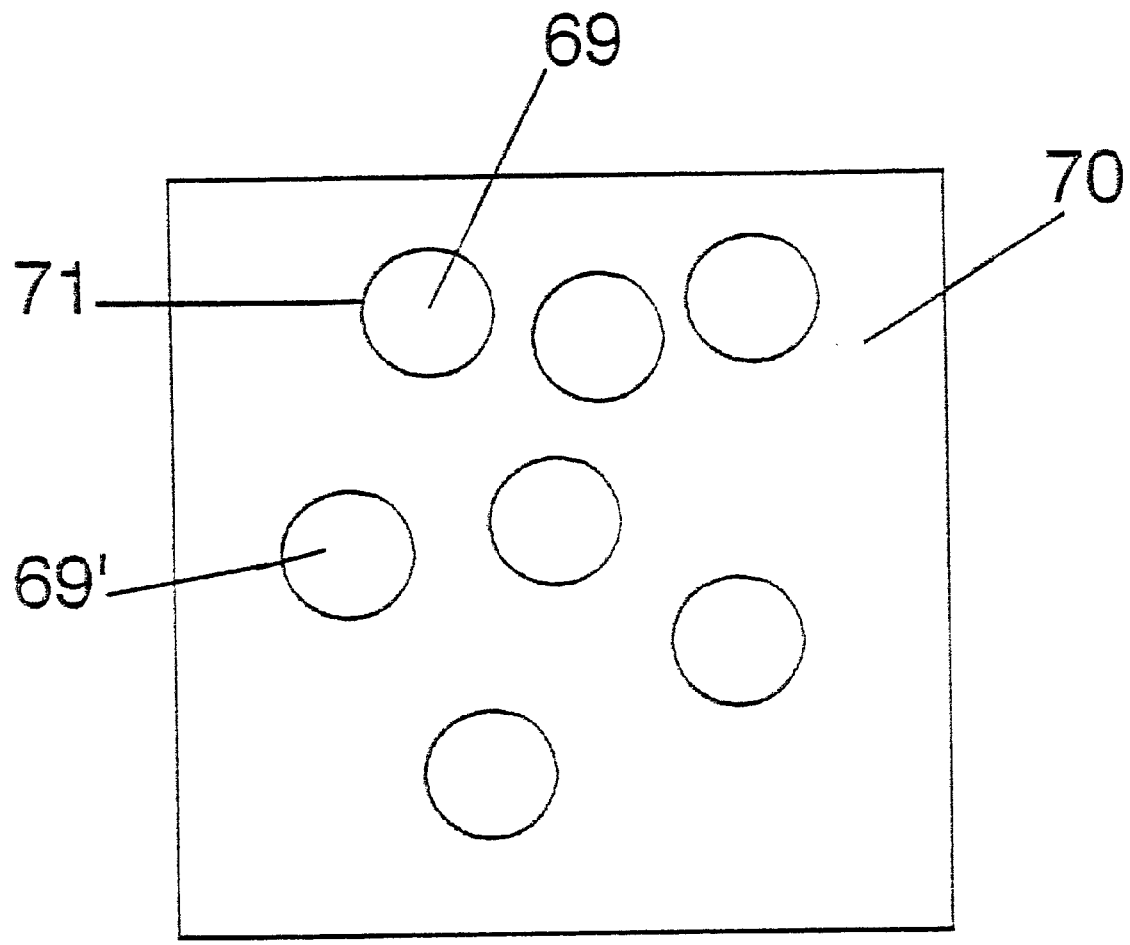

FIG. 12 is a schematic view of reaction system according to the present invention.

DETAILED DESCRIPTION OF THE INVENTION

The reaction according to the present invention is shown thusly:

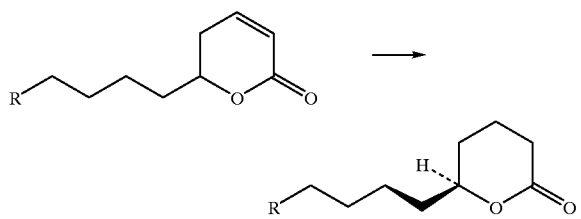

wherein R is methyl or n-propyl.

More specifically, the reaction involving oxidative growth concerns (i) maintenance of sufficiently low dextrose levels in the reaction medium and (ii) the use of an oxygen-containing gas such as air or oxygen which is dissolved in a relatively high amount into the reaction medium. In the process, which produces the optical isomer of our invention, the yeast species that is preferably used is *Saccharomyces cerevisiae*. However, other yeast species of Saccharomyces can be used to obtain comparable results.

The process is carried out by first introducing an inoculum of the selected yeast species into a reaction vessel which contains a production medium, typically including glycine or other equivalent nutrient source, a buffering agent such as $KH_2PO_4$, a yeast extract and other nutrient sources which may include trace minerals and growth factors.

Immediately subsequent to the introduction of the inoculum, a source of dextrose in a suitable nutrient medium is begun feeding into the reaction vessel (and throughout the entire fermentation procedure).

Up to about 30 hours after inoculation, a mixture of the unsaturated olide compound, namely, 2-decen-1,5-olide or 2-dodecen-2,5-olide and a fatty acid ester (the organic phase) (or substitute therefor as set forth, infra) is pumped into the reaction vessel.

A particularly suitable fatty acid ester is NEOBEE® Oil which is a triglyceride of $C_8$–$C_{10}$ fatty acids. Other suitable fatty acid esters can be used for this purpose, for example, olive oil, castor oil, safflower oil, soybean oil and the like. In place of the triglycerides, high molecular weight hydrocarbons such as hexadecane and tetradecane can be used. The mixture of the unsaturated olide compound and the fatty acid ester (or substitute therefor) constitutes the second liquid organic phase. The triglyceride (or substitute therefor) functions, inter alia, as the organic phase former and keeps the substrate separated from the yeast.

It must be emphasized that the product and substrate are each toxic to the microorganism (e.g., Saccharoyces). Accordingly, our novel two-phase process gives rise to a diminution of such toxicity, thus resulting in a surprisingly substantial increase in product yield and conversion. Such diminution of toxicity is created by the low partition coefficient between the two phases: the organic phase containing relatively high concentrations of olide reactant and product; and the aqueous phase containing the microorganism, the actual reaction taking place proximate the phase interface.

Furthermore, our novel two-phase fermentation surprisingly reduces the cost of product recovery. The organic phase-containing product is easily separable from the aqueous phase by a simple procedure, i.e., the use of a centrifuge or other simple phase separation techniques. The product is recovered from the organic phase by means of routine distillation, and the triglyceride (or substitute therefor) is recycled, thus giving rise to an environmental advantage. Our approach eliminates the high cost of extraction using an environmentally unacceptable organic solvent and substantially eliminates all environmental safety issues and health hazards that are associated with the use of such environmentally unacceptable organic solvents.

The nutrient feed, which contains the dextrose and may also contain a solution of vitamins as desired and trace mineral solutions as desired as well as buffers and the like, is pumped into the reaction vessel.

It is to be understood that the production medium and the nutrient medium suitable for the present invention are well known and understood by persons skilled in the art.

The fermentation reaction is permitted to proceed, being careful to maintain oxidative growth conditions in the reaction vessel by balancing dextrose feed and oxygen injection into the system. Thus, the concentration of the dextrose is maintained at least about 0.01 grams per liter to as much as 1.5 grams per liter, preferably 0.1 up to 0.5 grams per liter, most preferably at about 0.03–0.07 grams per liter during the fermentation reaction. The preferred operable range of dextrose concentrations during the fermentation is a function of the specific Saccharomyces organism species or strain used. The actual dextrose concentration varies at any given time from a minimum to a maximum, recognizing that too high a dextrose concentration will result in fermentative growth and production of ethyl alcohol, resulting in a lower biomass production (giving rise to much lower product yield and conversion). By automatic addition of the nutrient feed, the nutrient feed rate can range from about 5 to about 72 grams per liter per hour.

The desired temperature of the reaction is approximately 30° C., although this can vary as will be understood by persons skilled in this art. The optimum temperature of the reaction can be readily determined by skilled operators using parameters well understood in the fermentation art. A typical range of temperature is 20 to 50° C. It is a feature of the fermentation reaction of the present invention to avoid the formation of excessive amounts of alcohol which is typically produced in prior known methods. Under the reaction conditions discovered by applicants, unwanted alcohol production is avoided by a control of the dextrose addition and charging of the oxygen source to the system. Thus, the rate of dextrose addition and oxygen (or air) addition is such as to maintain oxidative growth in the reaction medium, avoiding the formation of excessive $C_2H_5OH$ and enabling the substrate, namely, the unsaturated olide compound, to slowly diffuse out of the organic phase into the aqueous phase and thereby control the reaction to form the saturated olide compound product as discussed, supra.

As an example of oxygen in the system, the oxygen is introduced at a rate which is at least about 0.1 liters per liter of reaction mixture. The injection of air or other oxygen-containing gas is controlled so as to measure at least 10% dissolved oxygen as measured by a standard oxygen probe at all times during the reaction.

The resulting products in the form of mixtures of saturated lactones or as separate lactones or groups of lactones are useful in augmenting or enhancing the aroma or taste of consumable materials as set forth herein.

The form in which the microorganism Saccharomyces yeast is used is not critical. It can be used as a culture in a suspension, including the cells and the corresponding nutrient solution or in the form of cells suspended in a buffering solution. The cells or an enzyme extract thereof may be immobilized on a suitable solid support which may then be used to effect the transformation.

The culture suspension is prepared by inoculation of a suitable medium with the microorganism. A suitable medium is one which contains carbon sources, nitrogen sources, inorganic salts and growth factors. Among the suitable carbon sources are, for example: glucose, galactose, L-sorbose, maltose, sucrose, cellobiose, trehalose, L-arabinose, L-rhamnose, ethanol, glycerol, L-erythritol, D-mannitol, lactose, melibiose, raffinose, melezitose, starch, D-xylose, D-sorbitol, α-methyl-D-glucoside, lactic acid, citric acid and succinic acid. Among the suitable nitrogen sources are, for example: nitrogen containing organic substances such as peptone, meat extract, yeast extract, corn steep liquor, casein, urea, amino acids; or nitrogen containing inorganic compounds such as nitrates, nitrites and inorganic ammonium salts. Among the suitable inorganic salts are, for example: phosphates of magnesium, potassium, calcium and sodium. The above-mentioned nutrients in the culture medium may be supplemented with, for example: one or more vitamins of the B group and/or one or more trace minerals such as Fe (iron), Mo (molybdenum), Cu (copper), Mn (manganese) and B (boron) as desired. However, the process can be performed in a vitamin-free medium, for example, when a small amount of yeast extract is added to the medium there is no need for vitamins or trace minerals.

The cultivation of the microorganism can be carried out as a stationary culture or as a submerged culture (e.g., shaking culture, fermenters), preferably under aerobic conditions. One suitably may work in the pH range of from about 3.5 to about 8.0 and preferably in the range of from about 4.0 to about 7.5. The pH may be regulated by the addition of inorganic or organic bases, such as aqueous or gaseous ammonia, sodium hydroxide, potassium hydroxide, calcium hydroxide, calcium carbonate; by ion-exchange resins; or by the addition of a buffer such as phosphate or phthalate. The incubation temperature is suitably maintained at between about 15° C. and about 33° C., with the range from about 20° C. to about 30° C. being preferred.

The process in accordance with the invention is conveniently carried out by adding a source of sugar such as dextrose to the culture medium at the onset of cultivation as the carbon source. Alternatively, the dextrose may be added in combination with another carbon source, as mentioned above, either during cultivation or when the cultivation is complete. The amount level or concentration of the substrate in the medium may vary. For example, in the case of sources of dextrose, levels of from about 0.3% to about 5% may make up the medium initially or be added during the course of the oxidative growth, although the specific level of dextrose source may be easily determined and can be varied.

The reaction time may vary depending on the composition of the culture medium and the substrate concentration. In general, shaking flask cultures requires from between about 2 hours and about 240 hours, depending upon the microorganism and the composition of the culture medium. However, when a fermenter vessel is used, the oxidative reduction reaction time may be reduced to about 100 hours or less.

The reaction of this invention may be carried out using the cells of the yeast microorganism isolated from the culture solution or with an enzyme extract isolated from the cells in a manner known, per se. The yeast cells may be immobilized on a solid support and the desired transformation effected in the absence of the live yeast microorganism. The transformation of the substrate may be effected by mutants of the yeast microorganism. Such mutants can be obtained readily by methods well known in the art, for example, by exposing the yeast cells to UV or X-rays or customary mutagenic substances such as, for example, acridine orange.

The substrate, which is the unsaturated olide compound, is generally added directly to the production medium. Sources for the 2-decen-1,5-olide or the 2-dodecen-1,5-olide can vary, but it has been found that a particularly suitable source for the purposes of this invention is Massoi bark oil and, more particularly, a Massoi lactone $C_{10}$ fraction for the source of 2-decen-1,5-olide. The Massoi lactone $C_{12}$ fraction is a preferred source for the 2-dodecen-1,5-olide. Particularly suitable materials are sold by Haldin International Inc. of Closter, N.J. One such product is natural 2-decenoic δ-lactone (GRAS) FEMA No. 3744, which is a pale yellow liquid with a dry, musty coconut, creamy flavor and aroma with a refractive index of 1.467–1.477 and a molecular weight of 168. It is insoluble in water and soluble in alcohol with a specific gravity of 0.982–0.992.

Also available from Haldin is a natural fractionated Massoi bark oil, FEMA No. 3747, which is a mixture of 2-decenoic, 2-dodecenoic and 2-tetradecenoic δ-lactones. The appearance is a pale yellow liquid with a fruity, oily coconut, creamy flavor and aroma. The mixture is also insoluble in water and soluble in alcohol.

The triglyceride (or substitutes therefor) is added to the production medium with the unsaturated olide to form the organic phase. The triglyceride controls the rate of diffusion of the unsaturated olide and saturated olide product into the aqueous phase in such a way that the toxicity of substrate and product to the microorganism is substantially eliminated. Triglycerides of $C_8$–$C_{10}$ fatty acids as well as vegetable oils and substitutes therefor cited, supra, are well suited for this purpose, including the specific NEOBEE® oil.

Conventional antifoam agents such as silicone oils (e.g., UCON®), polyalkyleneglycol derivatives, maize oil or soya oil can be used to control foaming as is known in the art.

The saturated lactone compounds obtained in accordance with the present invention and one or more auxiliary perfume ingredients including, for example: hydrocarbons, alcohols, ketones, aldehydes, nitriles, esters, ethers, synthetic essential oils, lactones other than those of our invention and natural essential oils, may be admixed so that the combined odors of the individual components produce a pleasant and desired fragrance, particularly and preferably in the fruity area (e.g., peach and apricot aromas). Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low-boiling, fresh-smelling materials.

In perfume compositions, it is the individual compositions which contribute to their particular olfactory characteristics; however, the overall sensory effect of the perfume composition will be at least the sum total of the effects of each of the ingredients. Thus, one or more of the lactone derivative (s) of our invention can be used to alter, modify or enhance the aroma characteristics of a perfume composition, for example, by utilizing or moderating the olfactory reaction contributed by another ingredient in the composition.

The amount of lactone derivative(s) of our invention, which will be effective in perfume compositions as well as in perfumed articles and colognes, depends upon many factors including the other ingredients, their amounts and the effects which are desired. It has been found that perfume compositions containing as little as 0.005% of lactone derivative(s) or even less (e.g., 0.0025%) can be used to impart sweet, fresh fruity, peach aromas with sweet, creamy, nut-like topnotes and heavy fruity and peach undertones to soaps, cosmetics, detergents including anionic, cationic, nonionic and zwitterionic solid or liquid detergents, perfumed polymers and other products. The amount employed can range up to 70% of the fragrance components and will depend upon the consideration of cost, nature of the end product, the effect desired on the finished product and the particular fragrance sought.

The saturated lactone compounds of this invention are useful when either taken alone or taken together with other perfumery ingredients in detergents, soaps, space odorants and deodorants, perfumes, colognes, toilette waters, bath preparations, hair preparations such as lacquers, brilliantines, pomades and shampoos; cosmetic preparations such as creams, deodorants, hand lotions and sun screens; powders such as talcs, dusting powders, face powders and the like.

As little as 0.25% of the saturated lactone compound can suffice to impart intense, substantive, sweet, fresh fruity, peach aroma with sweet creamy and nut-like topnotes and heavy fruity and peach undertones to floral and patchouli perfume formulations. Generally, no more than 5% of the saturated lactone compound based on the ultimate end product is required to be used in the perfume compositions.

Furthermore, as little as 0.25% of the lactone can suffice to impart such aromas to perfumed articles, per se, whether in the presence of other perfume materials or whether used by themselves. Thus, the range of use of the saturated lactone compounds of this invention in perfumed articles, e.g., perfumed polymers and solid or liquid anionic, cationic, nonionic or zwitterionic solid or liquid detergents, may vary from 0.25% up to about 5% by weight based on the total weight of the perfumed article.

In addition, the perfume composition or fragrance composition of our invention can contain a vehicle or carrier for the lactone compounds. The vehicle can be a liquid such as a nontoxic alcohol (e.g., ethanol; a nontoxic glycol, e.g., propylene glycol or the like). The carrier can also be an absorbent solid such as gum (e.g., gum arabic, xanthan gum or guar gum) or components for encapsulating the composition by means of coacervation (such as by gelatin) or by means of the formulation of a polymer around a liquid center. This can be accomplished by using a urea formaldehyde prepolymer to form a polymeric capsule around a perfume composition center as is known in the art.

It will be appreciated from the present disclosure that the saturated lactone compounds according to the present invention can be used to alter, vary, fortify, modify, enhance or otherwise improve the flavor of a wide variety of materials which are ingested, consumed or otherwise organoleptically sensed.

The terms "alter" and "modify" in their various forms will be understood herein to mean the supplying or imparting of a flavor character or note to an otherwise bland, relatively tasteless substance or augmenting an existing flavor characteristic where the natural flavor is deficient in some regard or supplement the existing flavor impression to modify its organoleptic character.

The term "enhance" is intended herein to mean the intensification (by use of the saturated lactone compound of this invention) of a flavor, aroma note or nuance in a foodstuff, perfume composition or perfumed article without changing the quality of said note or nuance.

A "flavoring composition" as referred to herein means one which contributes a part of the overall flavor impression by supplementing or fortifying a natural or artificial flavor in a material or one which supplies substantially all the flavor and/or aroma character to a consumable article.

The term "foodstuff" as used herein included both solid and liquid ingestible material for man or animals, which materials usually do, but need not have nutritional value. Thus, foodstuffs include meats; gravies; soups; convenience foods; malt; alcoholic and other beverages; milk and dairy products; seafood including fish, crustaceans, mollusks and the like; candies; vegetables; cereals; soft drinks; snacks; dog and cat foods; other veterinary products and the like.

When the saturated lactone compounds of this invention are used in a flavoring composition, they can be combined with conventional flavoring materials or adjuvants. Such co-ingredients or flavoring adjuvants are well known in the art for such and have been extensively described in the literature. Requirements of such adjuvant materials are:

(1) that they be nonreactive with the lactone compound(s) of this invention;

(2) that they be organoleptically compatible with the lactone compound(s) of this invention whereby the flavor of the ultimate consumable material to which the lactone compounds are added is not detrimentally affected by the use of the adjuvant; and (3) that they be ingestible, acceptable and thus nontoxic or otherwise nondeleterious.

Apart from these requirements, conventional materials can be used and broadly include other flavor materials, vehicles, stabilizers, thickeners, surface active agents, conditioners and flavor intensifiers.

Such conventional flavoring materials include saturated fatty acids; unsaturated fatty acids and amino acids; alcohols including primary and secondary alcohols; esters; carbonyl compounds including ketones and aldehydes; lactones (other than the lactones of our invention); other cyclic organic materials including benzene derivatives, alicyclic compounds, heterocyclics such as furans, pyridines, pyrazines and the like; sulfur-containing compounds including thiols, sulfides, disulfides and the like; proteins; lipids;

carbohydrates; so-called flavor potentiators such as monosodium glutamate, magnesium glutamate, calcium glutamate, guanylates, and inosinates; natural flavoring materials such as cocoa, vanilla and caramel; essential oils and extracts such as anise oil, clove oil and the like; and artificial flavoring materials such as vanillin and the like.

Specific preferred flavor adjuvants are as follows:

anise oil;
ethyl-2-methyl butyrate;
vanillin;
cis-3-heptenol;
cis-3-hexenol;
trans-2-heptenol;
cis-3-heptenal;
butyl valerate;
2,3-diethyl pyrazine;
methyl cyclopentenolone;
benzaldehyde;
valerian oil;
3,4-dimethoxyphenol;
amyl acetate;
amyl cinnamate;
γ-butyryl lactone;
furfural;
trimethyl pyrazine;
phenyl acetic acid;
isovaleraldehyde;
ethyl maltol;
ethyl vanillin;
ethyl valerate;
cocoa extract;
coffee extract;
peppermint oil;
spearmint oil;
clove oil;
anethol;
cardamom oil;
wintergreen oil;
cinnamic aldehyde;
ethyl-2-methyl valerate;
γ-hexenyl lactone;
2,4-decadienal;
2,4-heptadienal; and
butylidene phthalide.

DETAILED DESCRIPTION OF THE DRAWINGS

The accompanying GLC profiles illustrate products obtained by carrying out the procedures described in the examples and show slightly different peaks which represent differences in yield.

Figure 1:
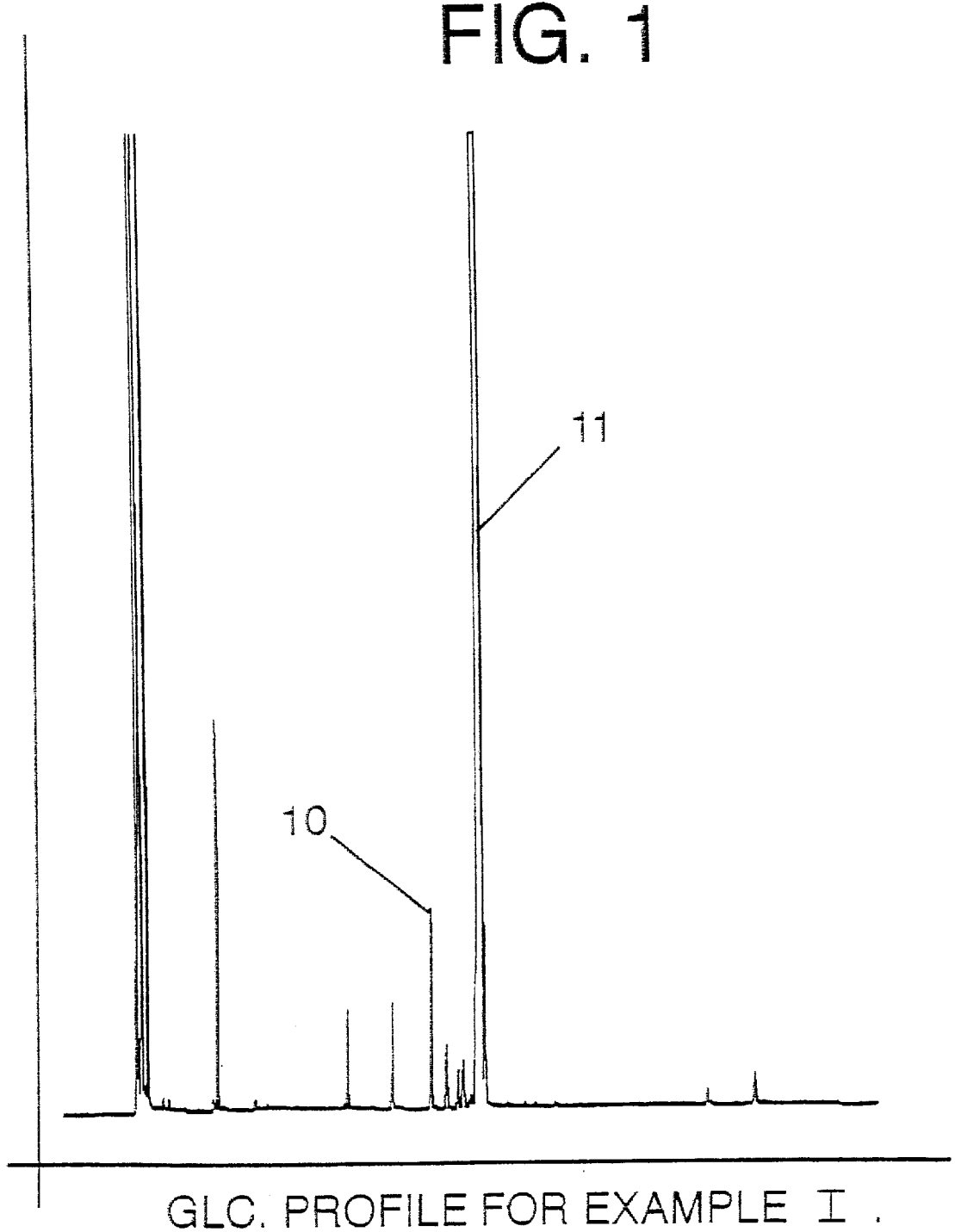
FIG. 1 is a GLC profile of the reaction product for Example I containing the compound having the structure.

FIG. 1 is a GLC profile for the reaction product of Example I. The peak indicated by reference numeral 10 is the peak for the compound having the structure:

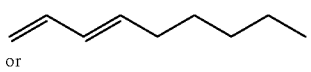
or

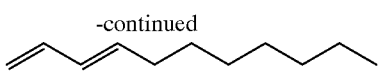

which are impurities in the starting material.

The peak indicated by reference numeral 11 is the peak for the compound having the structure:

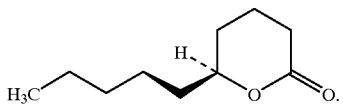

Figure 2:
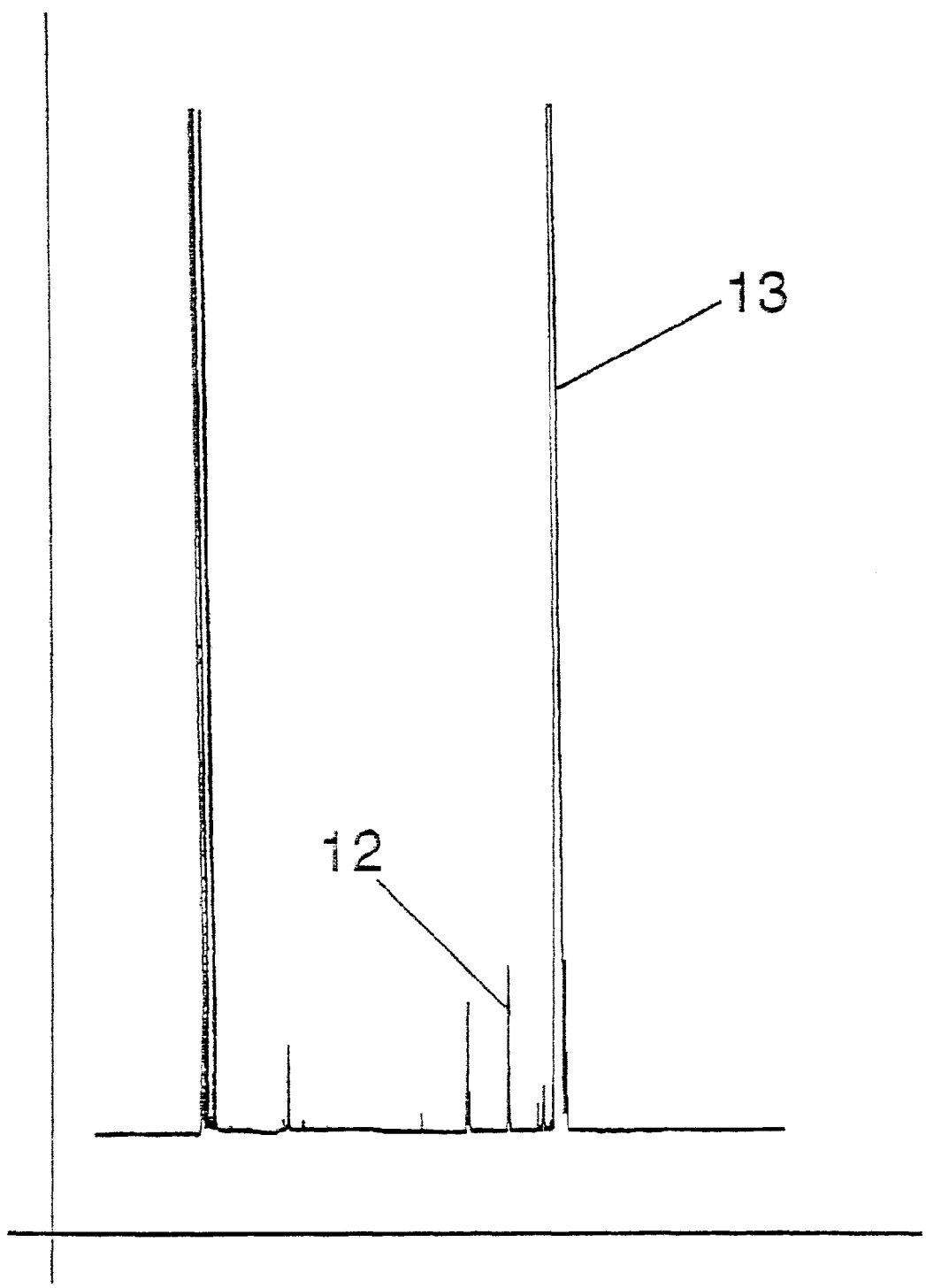
FIG. 2 is a GLC profile for the reaction product of Example II containing the compound having the structure.

FIG. 2 is a GLC profile for the reaction product of Example II. The peak indicated by reference numeral 12 is the peak for the compound having the structure:

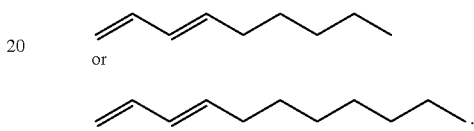

The peak indicated by reference numeral 13 is the peak for the compound having the structure:

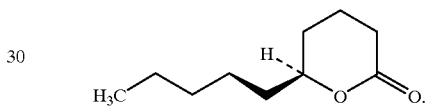

FIG. 3 is the GLC profile for the reaction product of Example III. The peak indicated by reference numeral 14 is for the compound having the structure:

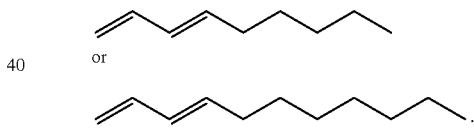

The peak indicated by reference numeral 15 is for the compound having the structure:

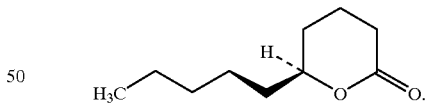

FIG. 4 is the GLC profile for the reaction product of Example IV. The peak indicated by reference numeral 16 is for the compound having the structure:

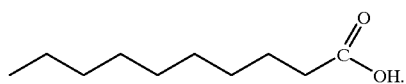

The peak indicated by reference numeral 17 is for the compound having the structure:

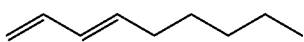

-continued or

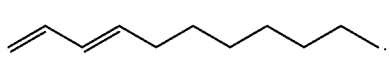

The peak indicated by reference numeral 18 is for the compound having the structure:

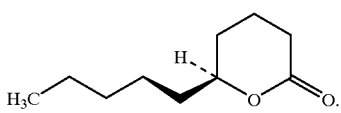

FIG. 5 is a GLC profile for the reaction product of Example V. The peak indicated by reference numeral 19 is for the compound having the structure:

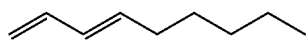

or

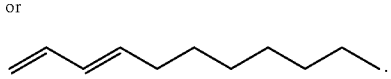

The peak indicated by reference numeral 20 is for the compound having the structure:

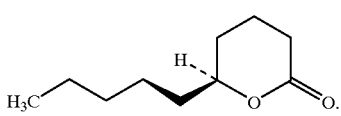

FIG. 6 is the GLC profile for the reaction product of Example VI using a Massoi $C_{12}$ fraction. The peak indicated by reference numeral 21 is for the compound having the structure:

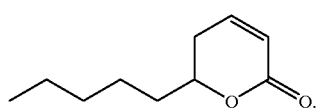

The peak indicated by reference numeral 22 is for the compound having the structure:

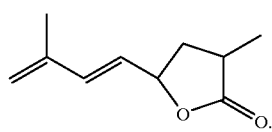

The peak indicated by reference numeral 23 is for the compound having the structure:

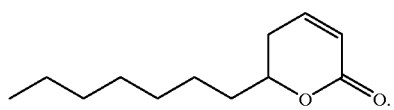

The peak indicated by reference numeral 24 is for the compound having the structure:

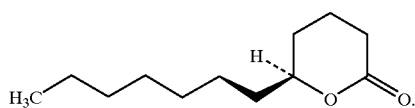

FIG. 7 is the mass spectrum for the Massoi bark oil starting material used in Example I. The peak indicated by reference numeral 25 is the compound having the structure:

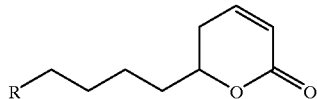

where $R=CH_3$.

The peak indicated by reference numeral 26 is for the compound having the structure:

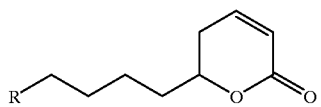

where R=n-propyl.

The peak indicated by reference numeral 27 is for the compound having the structure:

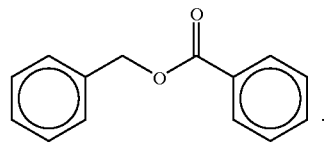

FIG. 8 is the mass spectrum for the Massoi bark oil starting material used in Example I. The peak indicated by reference numeral 28 is for the compound having the structure:

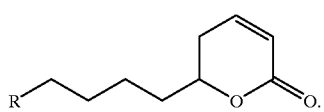

The peak indicated by reference numeral 29 is for the compound having the structure:

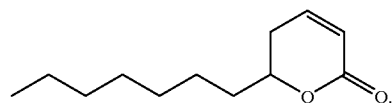

The peak indicated by reference numeral 30 is for the compound having the structure:

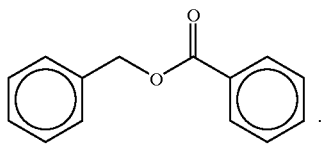

The peak indicated by reference numeral 31 is for the compound having the structure:

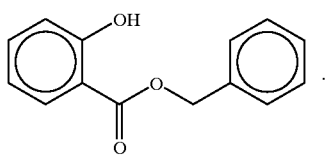

The GC mass spectrum in FIG. 7 was prepared from a methyl silicon column 50 meters in height by 0.32 mm using 0.5 micron-bonded, fused silica, operated at an initial temperature of 75° C. up to a final temperature of 225° C. at 2° C. per minute for a total time of 30 hours.

The GC mas spectrum column for FIG. 8 is a CARBO-WAX® 20M column 50 meters×0.32 mm using 0.3 micron nonbonded, fused silica with the temperature range of from 75° C. up to 225° C. at a rate of 2° C. per minute for a total time of 30 hours.

FIG. 9 is a mass spectrum for the Massoi bark oil used in Example I.

FIG. 10 is a mass spectrum for the starting material Massoi bark oil. The peak indicated by reference numeral 32 is for the compound having the structure:

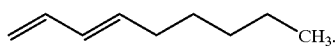

The peak indicated by reference numeral 33 is for the compound having the structure:

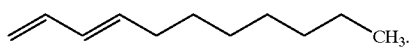

The peak indicated by reference numeral 34 is for the compound having the structure:

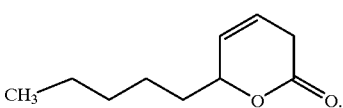

The peak indicated by reference numeral 35 is for the compound having the structure:

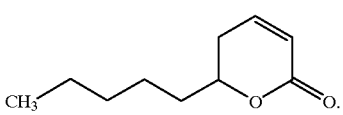

The peak indicated by reference numeral 36 is for the compound having the structure:

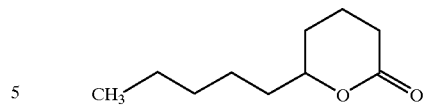

(which represents a mixture of isomers having the structures:

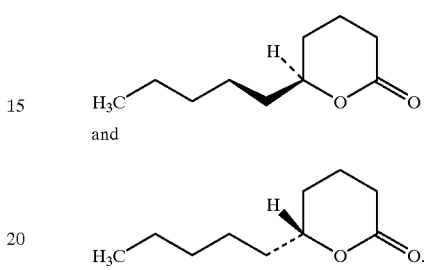

The peak indicated by reference numeral 37 is for the compound having the structure:

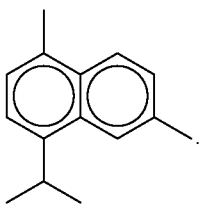

FIG. 11 is a mass spectrum total ion chromatogram (TIC) of the distillation fraction 2 of Example I. The peak indicated by reference numeral 38 is for the compound having the structure:

The peak indicated by reference numeral 39 is for the compound having the structure:

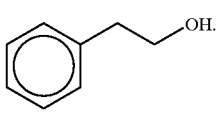

The peak indicated by reference numeral 40 is for the compound having the structure:

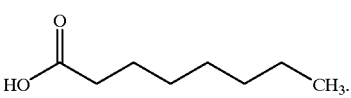

The peak indicated by reference numeral 41 is for the

The peak indicated by reference numeral 42 is for the compound having the structure:

[structure: phenethyl group]

FIG. 11A is an expanded TIC of section A in FIG. 11. The peak indicated by reference numeral 43 is for the compound having the structure:

[structure: acetone]

The peak indicated by reference numeral 44 is for the compound having the structure:

[structure: isoamyl alcohol]

The peak indicated by reference numeral 45 is for the compound having the structure:

[structure: 3-methyl-2-butanol]

The peak indicated by reference numeral 46 is for the compound having the structure:

[structure: 1,3-butanediol type]

The peak indicated by reference numeral 47 is for the compound having the structure:

[structure: phenol]

FIG. 11B is an expanded TIC of section B of FIG. 11. The peak indicated by reference numeral 48 is for the compound having the structure

[structure: cresol] (ortho, meta or para isomer).

The peak indicated by reference numeral 49 is for the compound having the structure:

[structure: 2-phenylethanol]

The peak indicated by reference numeral 50 is for the compound having the structure:

[structure: 2-phenylethanol]

The peak indicated by reference numeral 51 is for the compound having the structure:

[structure: methylphenol] (ortho or para isomer).

FIG. 11C is an expanded TIC of section C of FIG. 11. The peak indicated by reference numeral 52 is for the compound having the structure:

[structure: indole]

The peak indicated by reference numeral 53 is for the compound having the structure:

[structure: phenylcyclohexane/phenylcyclohexene mixture]

(a mixture wherein in the mixture in each of the compounds, one of the dashed lines is a carbon-carbon single bond and the other of the dashed lines is a carbon-carbon double bond).

The peak indicated by reference numeral 54 is for the compound having the structure:

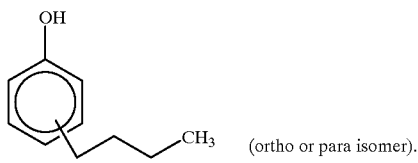
(ortho or para isomer).

The peak indicated by reference numeral 55 is for the compound having the structure:

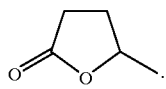

The peak indicated by reference numeral 56 is for the compound having the structure:

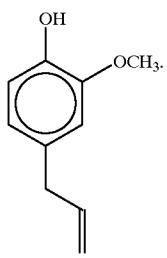

The peak indicated by reference numeral 57 is for the compound having the structure:

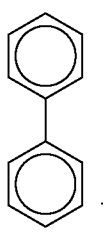

The peak indicated by reference numeral 58 is for the compound having the structure:

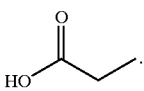

The peak indicated by reference numeral 59 is for the compound having the structure:

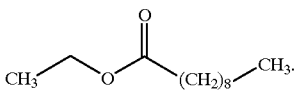

The peak indicated by reference numeral 60 is for the compound having the structure:

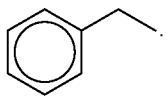

The peak indicated by reference numeral 61 is for the compound having the structure:

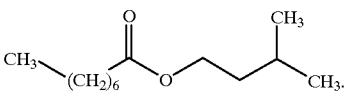

FIG. 11D is an expanded TIC of section D of FIG. 11. The group of peaks indicated by reference numeral 62 is for sesquiterpenes.

The peak indicated by reference numeral 63 is for the compound having the structure:

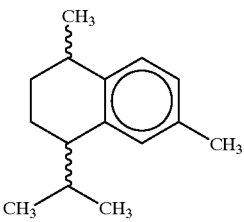

(indicative of a mixture of stereoisomers).

The peak indicated by reference numeral 64 is for the compound having the structure:

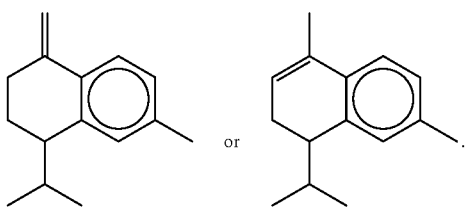

The peak indicated by reference numeral 65 is for sesquiterpene alcohol.

The peak indicated by reference numeral 66 is for the compound having the structure:

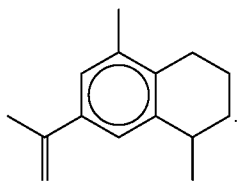

The peak indicated by reference numeral 67 is for the compound having the structure:

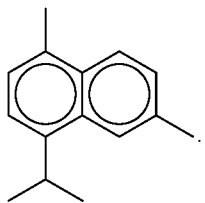

The peak indicated by reference numeral 68 is for the compound having the structure:

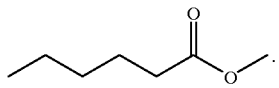

FIG. 12 is a schematic micro representation of the two-phase system of the invention wherein the organic phase indicated by the globules of the substrate-glyceride 69; 69 is admixed with the aqueous nutrient phase 70. The interface 71 is the boundary across which the substrate passes to enter into the controlled oxidative reaction conditions to produce the desired products.

EXAMPLE I

Using a 35 liter fermenter vessel of conventional configuration, the following production medium was prepared in the total amount of 12 liters:

| Ingredients | g/L |
| --- | --- |
| Glycine | 5.0 |
| $KH_2PO_4$ | 11.0 |
| $MgSO_4.7H_2O$ | 3.0 |
| NaCl | 0.1 |
| Yeast extract | 5.0 |
| Inositol | 0.1 |

A trace mineral solution stock was prepared as follows:

| Ingredients | g/L |
| --- | --- |
| $FeCl_3.6H_2O$ | 45.0 g |
| $CoCl_2$ | 2.0 g |
| $CaCl_2$ | 1.0 g |
| Boric acid | 0.5 g |
| Sodium citrate | 73.5 g |
| $ZnCl_2$ | 2.0 g |
| Sodium molybdate dihydrate | 2.35 g |
| $CuSO_4.5H_2O$ | 3.0 g |
| $MnCl_2$ | 1.6 g |
| Deionized water | 1.0 L |

A vitamin solution stock was prepared as follows:

| Ingredients | g/L |
| --- | --- |
| Biotin | 0.1 g |
| Folic acid | 0.1 g |
| Riboflavin | 0.5 g |
| Pyridoxine HCl | 1.40 g |

-continued

| Ingredients | g/L |
| --- | --- |
| Pantothenic acid | 5.50 g |
| Niacin | 6.10 g |
| 50% NaOH | 5.0 ml |
| Deionized water | 1.0 L |

The vitamin solution stock and trace mineral solution stock were mixed as follows:

| Ingredients | g/L |
| --- | --- |
| Vitamin solution stock | 5.4 ml |
| Trace mineral solution stock | 5.4 ml |
| 10% Thiamine HCl | 0.54 ml |
| $CaCl_2.2H_2O$ | 0.2 |

The inoculum used for introduction into the production medium described above was 2% FERMIPAN® yeast, which is a dry baker's yeast, *Saccharomyces cerevisiae*.

The temperature was adjusted to 30° C. and aeration begun to provide 0.42 liters of oxygen per liter of reaction mixture. Agitation was set at 700 rpm.

A mixture was then prepared as the organic phase containing 49 grams of 2-decene-1,5-olide (Massoi lactone $C_{10}$ fraction obtained from the Haldin Company) and 432 grams NEOBEE® oil, which is a triglyceride of a $C_8$–$C_{10}$ fatty acid.

A nutrient feed identified as follows was prepared:

| Ingredients | g/L |
| --- | --- |
| $KH_2PO_4$ | 11.0 |
| $MgSO_4.7H_2O$ | 3.0 |
| NaCl | 0.2 |
| Yeast extract | 5.0 |
| Inositol | 0.2 |
| Vitamin solution | 5.4 ml |
| Trace mineral solution | 5.4 ml |
| 10% Thiamine HCl | 0.54 ml |
| $CaCl_2.2H_2O$ | 0.2 ml |

There was sterilized separately 500 grams of corn starch hydrolysate in the form of dextrose, identified as CERELOSE® 2001, obtained from Corn Products Inc. of Sumit-Argo, Ill.

The pH was maintained automatically at 5.5 with addition of 10% ammonium hydroxide ($N_4OH$) during fermentation.

In Example I, the fermenter reactor was inoculated with 2% of the FERMIPAN® yeast, which is a dry *Saccharomyces cerevisiae* yeast also known as baker's yeast. Nutrient (sugar) feed was commenced at the same time at 60 grams/hour. After 7 hours, the dissolved oxygen measured 68.5%, and 307 grams of the nutrient feed has been pumped. The solids were determined to be approximately 4.2%. The dissolved oxygen was measured by an oxygen probe.

At 7 hours, the Massoi/NEOBEE® oil mixture began pumping into the reactor at a rate of 1.5 gram/liter/hour. The sugar content measured 0.29 gram/liter.

After 13 hours, the solids measured 10.3% and the dissolved oxygen was determined to be 80.8%. All of the Massoi bark oil-NEOBEE® oil mixture was pumped in by that point in time.

After 19 hours, the solids content was 9.8% and the dissolved oxygen content was 83.8%. At that point, 1.669 kg of the nutrient feed had been pumped in and the sample showed 3.57 g/L of (+) δ-decalactone. At the end of 31 hours, the dissolved oxygen was 80.6%.

At the completion of the reaction at 47 hours, the solids were measured at 2% and the dissolved oxygen was determined to be 73.3%. The total nutrient feed that had been pumped in was 2.8 kg.

The crude product was determined to be 35.59 g/L and was then distilled. The distilled product was 6.01 g/L of which 49.1% was the product (+) δ-decalactone having the structure:

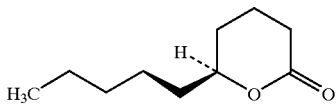

(2.95 g/L) ($[\alpha_D^{20}=+53.64°]$). The (+) δ-decalactone has an enantiomeric excess percent of 95.6 ($[\epsilon\epsilon\%=95.6]$). FIG. 1 shows the GLC profile of the results of Example I. The peak indictated by reference numeral 10 represents the compound having the formula:

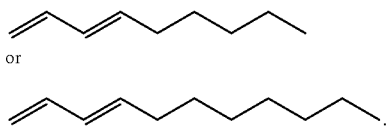

The peak represented by reference numeral 11 represents the compound having the structure:

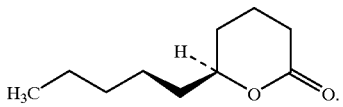

EXAMPLE II

The fermenter media and nutrient were the same as used in Example I, except that the inoculation was carried out at 1% concentration of the FERMIPAN® yeast. The nutrient was pumped at a rate of 38.2 grams/hour. Six hours after the inoculation, the total feed that had been pumped in was 547 grams, and the dissolved oxygen was 91% with the solid contents of 7.9%.

Seven hours after commencement of the run, the Massoi/NEOBEE® mixture began pumping into the fermenter reactor at a rate of 29 grams/hour. At 21.5 hours, the solids measured 9.7% and the dissolved oxygen was 72.4%. The total sugar pumped in at that point was 1.027 kg, and the amount of the Massoi substrate that had been pumped in was 120 grams.

At 24 hours, the sugar feeding rate was 82 grams/hour.

At 40 hours, the solids content was 8.6% with a dissolved oxygen of 74.4%. The sugar that had been pumped in at that point measured 2.573 kg with the total of the Massoi oil pumped in at 660.1 grams.

At 45.5 hours, the solids were determined at 8.9% with the dissolved oxygen of 88.6% and that the sugar pumped in was 2.863 kg. The total Massoi oil pumped in at that point was 705 grams.

At the completion of the reaction at 60 hours, solids measured at 8.3% with the dissolved oxygen of 94.1%. The sugar pumped in had amounted to 3.523 kg. The crude in the sample was 52.12 grams/liter. The distillate was 6.95 grams/liter. The percent product was 68.8% with a total yield of 4.79 grams/liter of (+) δ-decalactone having the structure:

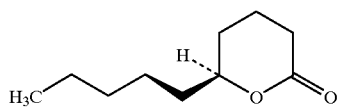

($[\alpha_D^{20}=+53.64°]$). The (+) δ-decalactone has an enantiomeric excess percent of 95.6 ($[\epsilon\epsilon\%=95.6]$).

FIG. 2 is the GLC profile of Example II and the peak indicated by reference numeral 12 represents the compound having the structure:

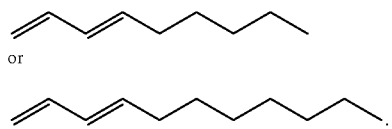

The peak indicated by reference numeral 13 represents the compound having the structure:

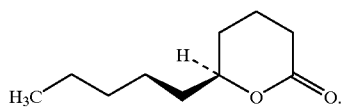

EXAMPLE III

Example III was carried out using the same fermenter media and nutrient feed as in Example II, except that the mixture of the Massoi lactone $C_{10}$ fraction of 2-decen-1,5-olide was 125 grams and the NEOBEE® oil was 1,125 grams. The production medium was inoculated with 1% FERMIPAN® yeast to provide a solids content at the start of the reaction of 3.5% with the dissolved air content at 100%.

The sugar feed was introduced at the beginning with a rate of 52.2 grams/hours.

After 18 hours, the mixture of the Massoi oil and the NEOBEE® oil was introduced at the rate of 30 grams/hour.

After 22.5 hours, the solids content rose to 12.1% with the dissolved oxygen of 72.9%. After 24 hours, the Massoi/NEOBEE® oil mixture was increased to 50 grams/hour, and the rpm of the stirrer was increased to 700 due to increased volume. The sugar feed continued pumping at 87.7 grams/hour. After 41 hours, the solids content measured 10.3% with the dissolved oxygen content of 80.4%. The total sugar pumped at this point was determined to be 29.20 kg, and the total Massoi oil pumped in at that point was 1,139.6 grams.

After 46.5 hours, the solids content was 9.6% and the dissolved oxygen was 85.6%. The sugar pumped up to that point was measured at 3.261 kg, and 1,200 grams of the Massoi oil was pumped in.

At the conclusion of the run at 65 hours, the dissolved oxygen measured at 98.7% and the total sugar that had been introduced was 4.025 kilograms. The crude product was determined to be 81.33 grams/liter with the distillate of 8.11 grams/liter. The percent product was 90.83% and the recovered amount of (+) δ-decalactone having the structure:

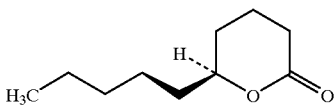

was 7.37 grams/liter. The total final fermenter volume was 17.25 liters and the total Massoil oil pumped had been 7.25 grams/liter.

FIG. 3 is a GLC profile of the product obtained from experiment 3. The peak indicated by the reference numeral 14 represents the compound having the structure with the formula:

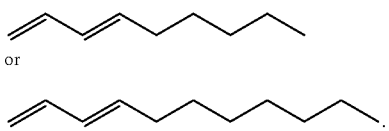

The peak represented by the reference numeral 15 represents a compound having the structure:

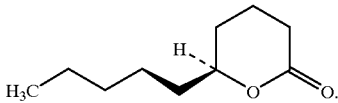

EXAMPLE IV

Using the same procedure, the same production medium and nutrient medium, the production of the saturated δ-decalactone was produced wherein the only difference was that the Massoi oil and the NEOBEE® oil mixture was added all at once, 16 hours after the inoculation. At 1.5 hours, the pumping of the sugar was at the rate of 56 grams/hour. After 17 hours, the solid content was determined to be 10.3% and the dissolved oxygen was measured by the oxygen probe at 83.7%. At this point, 877 grams of sugar had been pumped, which yielded a rate of 0.010 grams/liter of sugar.

At the time the Massoi oil/NEOBEE® oil mixture was added, the sugar pumping was at a rate of 61 grams/hour. At the 20th hour, the dissolved oxygen was determined by the probe to be at 81.5%. The sugar concentration was 0.176 grams/liter. The stirring was at a rate of 700 rpm. At 22.5 hours, the solid contents were determined to be 10.3% and the dissolved oxygen to be 83.7%. The sugar pumped at a rate of 1.25 kg. The rate of sugar was, therefore, determined to be 0.610 grams/liter. After 25.5 hours, the dissolved oxygen was 90.5% and the sugar feed was pumping at a rate of 40.6 grams/hour.

At the 41 hour interval, the dissolved oxygen was 106.7% with the solid contents of 8.6%. The sugar pumped so far was 2.035 kg and the rate of sugar addition was 0.642 grams/liter. At 46.5 hours, the sugar was determined to be 0.154 grams/liter and was pumping at the rate of 11 grams/hour. At that point, an additional 1% of the FERMIPAN® yeast was added.

At 65 hours, the solids content was 11.2% with the dissolved oxygen content content of 114%. The sugar was at a level of 0.040 grams/liter.

At 70.5 hours, the run was terminated and the total kilograms of nutrient feed was measured at 2.256 kg. Of the 125 grams of Massoil lactone added to the fermenter, 115.5 grams had been converted to (+) δ-decalactone for a total percentage of product 84.52%. The crude product was determined to be 84.13 grams/liter. The distilled product was found to be 8.82 grams/liter to give a product yield of 84.52%. Therefore, 7.45 grams/liter were converted to (+) δ-decalactone having the structure:

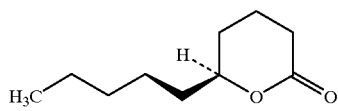

($[\alpha_D^{20}=+53.64°]$). The (+) δ-decalactone has an enantiomeric excess percent of 95.6 ($[\epsilon\epsilon\%=95.6]$).

FIG. 4 is the GLC profile of the product of Example IV. The peak indicated by reference numeral 16 represents the compound having the structure:

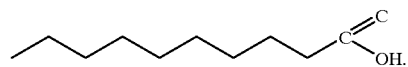

The peak indicated by reference numeral 17 represents a compound having the structure:

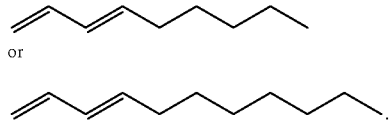

The peak represented by the index by the reference numeral 18 represents a compound having the structure:

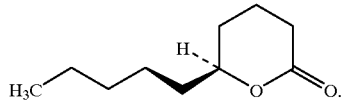

EXAMPLE V

In Example V, the run was conducted similar to Example III, with the following modification:

In this Example, the production medium was as follows:

| Ingredients | g/L |
| --- | --- |
| KH$_2$PO$_4$ | 10.0 g/L |
| MgSO$_4$.7H$_2$O | 3.0 g/L |
| NaCl | 0.1 g/L |
| TASTONE ® 900 | 5.0 g/L |
| Inositol | 0.1 g/L |
| Thiamine HCl solution (32.4 mg/L) | 0.54 ml/L 10% |
| Biotin solution (0.324 mg/L) | 1.35 ml/L 0.04% |
| CaCl$_4$.2H$_2$O | 0.2 g/L |

The nutrient feed was a 50% solution of the dextrose sold under the brand name CERELOSE® 2001.

The fermenter was inoculated with 1% FERMIPAN® yeast. After 2 hours, the dissolved oxygen was measured at 80.7 with the sugar pumping at the rate of 62 grams/hour. After 16.5 hours, the solids content was indicated as 9.4% with the dissolved air of 65.2%. The sugar content was 0.026 grams/liter and the total sugar pumped up to that time was 946 grams.

After 17 hours, the pumping of the Massoi oil-NEOBEE® oil mixture was commenced at a rate of 50 grams/hour.

At 21.5 hours, the solids content was determined to be 11.3% and the dissolved oxygen at 56.5%. The total sugar pumped at that point was 1.34 kg with the sugar content of 0.036 grams/liter. At that point, the yield of the (+) δ-decalactone was determined to be 0.413 grams/liter. At 24.5 hours, the dissolved oxygen was 58.4% and the sugar pumping at a rate of 92 grams/hour.

At 40 hours, the solids content was 8.4% with the dissolved oxygen content of 81.4% and the total amount of sugar pumped at that point was 2.916 kg. It was also determined that there was 4.25 grams/liter of (+) δ-decalactone having the structure:

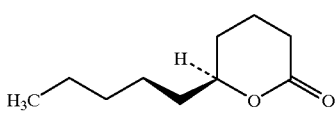

$[\alpha_D^{20}=+53.64°]$ present. The (+) δ-decalactone has an enantiomeric excess percent of 95.6 ([εε%=95.6]).

At 45.5 hours, the dissolved oxygen content was 90.7% and the total amount of sugar pumped at that point was 3.444 kg. The sugar content was 0.84 grams/liter and 4.87 grams/liter δ-decalactone were determined.

At the end of the run of 64 hours, a total of 3.84 kg nutrient had been added and the solids content was determined at 8.0% with the dissolved oxygen content of 101.6%. The sugar was determined to be 0.044 grams/liter. The crude product measured 75.87 grams/liter with the distilled decalactone product of 1269 grams distillate//liter with a purity of 56.3%. It was determined that 117.12 grams was converted to δ-decalactone having the structure:

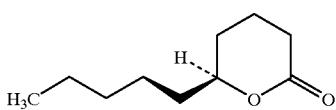

($[\alpha_D^{20}=+53.64°]$). A yield of 7.14 grams/liter of lactone with a purity of 99.5% was obtained. A 98% conversion was achieved.

EXAMPLE VI

Preparation of (+) δ-Dodecalactone

Reaction:

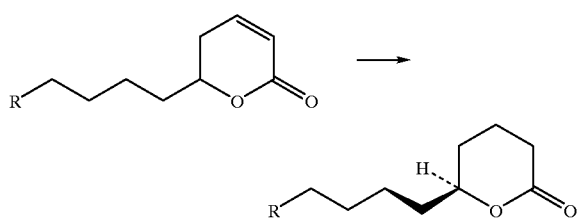

wherein R is n-propyl.

Example VI was carried out similar to Example V with the following modifications:

The fermenter reactive volume was 6 liters of broth in a 14 liter reaction vessel. The substrate material was 50% of the unsaturated compound 2-dodecen-1,5-olide. 30 Grams of 2-dodecen-1,5-olide ($C_{12}$ fraction) in 200 grams of NEOBEE® oil.

It was determined that after 41 hours, 47% was converted to the δ-decalactone product.

After 47 hours, it was determined that 58% had been converted, and after the final termination of the run at 60 hours, it was determined that 80% of the 2-dodecen-1,5-olide was converted to δ-dodecalactone.

FIG. 6 is a GLC profile of the products produced in Example VI. The peak indicated by reference numeral 21 represents the compound having the structural formula:

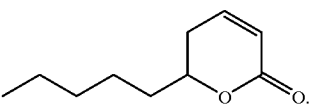

The peak indicated by reference numeral 22 represents the compound having the structural formula:

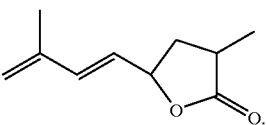

The peak indicated by reference numeral 23 represents the compound having the structure:

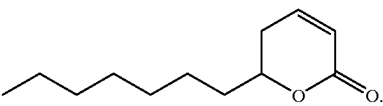

The peak indicated by reference numeral 24 represents the compound having the structural formula:

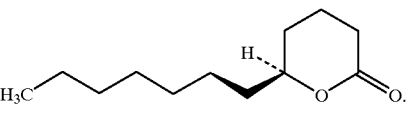

The following examples illustrate the use of the compounds of this invention as components in various compositions to augment or enhance those compositions.

EXAMPLE VII

The following mixture is prepared:

TABLE I

| | Parts by Weight | |
|---|---|---|
| Ingredients | VII (A) | VII (B) |
| Orange oil | 50 | 50 |
| Bergamot oil | 20 | 20 |
| Lime oil | 100 | 100 |
| Neroli oil | 5 | 5 |
| 4-(4-methyl-4-hydroxyamyl)δ-cyclohexene carboxaldehyde | 5 | 5 |
| 2,3,3A,4,5,7A-hexahydro-6,7A,8,8-tetramethyl-1,5,-methano-1H-inden-1-ol (prepared according to the process of Example 1 of U.S. Pat. No. 3,989,760) | 100 | 100 |

TABLE I-continued

| Ingredients | Parts by Weight | |
|---|---|---|
| | VII (A) | VII (B) |
| 1',2',3',4',5',6',7',8'-ocathydro-2',3',8',8'-tetramethyl-2'-acetonaphthone isomer mixture (produced according to the process of Example VII of U.S. Pat. No. 3,911,018) | 50 | 50 |
| γ-methyl ionone | 20 | 20 |
| 1-acetyl-2,5,5-trimethylcycloheptane (produced according to U.S. Pat. No. 389,411) | 50 | 50 |
| The compound prepared according to Example I having the structure: | 150 | 0 |

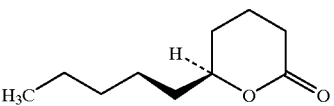

$((\alpha_D^{20} = +53.64°))$.

| The compound prepared according to Example VI having the structure: | | 150 |
|---|---|---|

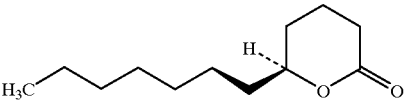

The lactone prepared according to Example I adds to this patchouli formulation a sophisticated, intense, substantive, peach-like aroma profile with sweet, creamy and nut-like topnotes and heavy fruity undertones; the extent of the substantivity and the strength being unexpected, advantageous and unobvious.

The compound of Example VI adds to this patchouli formulation a fresh, fruity aroma with peach undertones.

EXAMPLE VIII

Preparation of Soap Compositions

100 Grams of soap chip chips are produced according to Example V of U.S. Pat. No. 4,058,487, the specification for which is incorporated herein by reference as follows:

The sodium salt of an equal mixture of $C_{10}$–$C_{14}$ alkane sulfonate (95% active), 40 lbs, is dissolved in a mixture of 80 lbs of anhydrous isopropanol and 125 lbs of deionized water at 150° F. Into this mixture is dissolved 10 lbs of partially hydrogenated coconut oil, fatty acids and 15 lbs of sodium mono-$C_{14}$ alkyl maleate, and the pH of this solution is adjusted to 6.0 by the addition of a small amount of 50% aqueous solution of sodium hydroxide. The isopropanol is distilled off and the remaining aqueous solution is drum dried. The resulting solid actives are then blended in a chip mixture with 10 lbs of water, 0.2 lbs of titanium hydroxide and 0.7 lbs of one of the perfume ingredients as set forth in Table II, infra. The chips are then plodded into logs, cut to size and finally stamped into bars having a pH of approximately 6.9.

Each of the perfumed soaps produced by means of the foregoing procedure manifests an excellent aroma as set forth in Table II, infra:

TABLE II

| Ingredients | Fragrance Profile |
|---|---|
| The compound produced according to Example I. | A peach aroma with sweet, creamy, nut-like topnotes and heavy fruity undertones, with the advantage of having extended substantivity and high intensity |
| The compound prepared according to Example VI. | A fresh, fruity aroma with peach undertones, with the advantage of having extended substantivity and high intensity. |
| The perfume composition of Example VII(A) | A patchouli aroma with intense and substantive heavy fruity, peach-like undertones and sweet, creamy and nut-like topnotes. |
| The perfume composition of Example VII(B) | A patchouli aroma with intense and substantive fresh, fruity and pear undertones. |

EXAMPLE IX

Preparation of a Detergent Composition

A total of 100 grams of a detergent powder, prepared according to U.S. Pat. No. 4,058,472 (the specification for which is incorporated by reference herein), and containing 5% by $C_{14}$–$C_{18}$ alkyl catechol as a surface active component, the mixture being 60 parts by weight of mono-$C_{14}$–$C_{18}$ alkyl catechol, 35% sodium tetrapyrophosphate, 30% sodium silicate, 20% of sodium carbonate, 3% of sodium carboxymethyl cellulose and 7% of starch is mixed with 0.15 grams individually with each of the aroma ingredients set forth in Table II of Example VIII until a substantially homogeneous composition is obtained. Each of the compositions has an excellent aroma as set forth in Table II of Example VIII.

EXAMPLE X

Preparation of a Cosmetic Powder Composition

A cosmetic powder is prepared by mixing in a ball mill 100 grams of talcum powder with 0.25 grams of each of the perfume materials of Table II of Example VIII. Each of the powders has an excellent aroma as set forth in Table II of Example VIII.

EXAMPLE XI

Perfumed Liquid Detergent

Concentrated liquid detergents with aromas as set forth in Table II of Example VIII are prepared by adding 0.10%, 0.15% and 0.20% of each of the ingredients set forth in Table II of Example VIII. They are prepared by adding and homogeneously mixing the appropriate quantity of perfume substance of Table II of Example VIII in the liquid detergent. The detergents individually possess aromas as set forth in Table II of Example VIII, the intensity increasing with greater concentration of perfume substances as set forth in Table II of Example VIII.

EXAMPLE XII

Preparation of a Cologne Handkerchief Perfume

Each of the ingredients of Table II of Example VIII is incorporated individually into colognes of several strengths at concentrations of 2.0%, 2.5%, 3.0%, 3.5%, 4.0% and 5.0% in 75%, 80%, 85%, 90% and 95% aqueous ethanol; and into several concentrations of handkerchief perfumes at the rate of 15%, 20% and 25% (in 80%, 85%, 90% and 95% aqueous ethanol). Distinct and definite aromas as set forth in Table II of Example VIII are imparted to the colognes and to the handkerchief perfumes at the several concentrations as set forth above.

EXAMPLE XIII

100 Grams of soap chips (IVORY®, produced by the Procter & Gamble Company of Cincinnati, Ohio) are admixed with 1 gram of each of the substances as set forth in Table II of Example VIII, supra, until homogenous compositions are obtained. In each of the cases, the homogeneous compositions are heated under 3 atmospheres pressure at 180° C. for a period of 3 hours and the resulting liquids are placed into soap molds. The resulting soap cakes, on cooling, manifest excellent aromas as set forth in Table II of Example VIII.

EXAMPLE XIV

Preparation of Solid Detergent Compositions

Detergents are prepared from the following ingredients according to Example I of Canadian Patent No. 1,007,948, the specification for which is incorporated by reference herein:

| Ingredients | Parts by Weight |
| --- | --- |
| NEODOL ® 45-11 (a $C_{14}$–$C_{15}$ alcohol ethoxylated with 11 moles of ethylene oxide | 12 |
| Sodium carbonate | 55 |
| Sodium citrate | 20 |
| Sodium sulfate, water brighteners | q.s. |

The detergent is a "phosphate-free" detergent. A total of 100 grams of said detergent is admixed with 0.10, 0.15, 0.20 and 0.25 grams of each of the substances as set forth in Table II of Example VIII, supra. Each of the detergent samples has an excellent aroma as indicated in Table II of Example VIII.

EXAMPLE XV

Preparation of Drier-Added Fabric Softener Article

Utilizing the procedure of Example I at column 15 of U.S. Pat. No. 3,632,396, the specification for which is incorporated by reference herein, a non-woven cloth substrate useful as a drier-added fabric softening article of manufacture is prepared wherein the substrate, substrate coating, outer coating and the perfume material are as follows:

(1) a water "dissolvable" paper ("Dissolve Paper") as the substrate;
(2) ADOGEN® 448 (melting point about 140° F.) as the first substrate coating; and
(3) an outer coating having the following formulation (melting point about 150° F.):
   57% $C_{20}$–$C_2$ HAPS;
   22% isopropyl alcohol;
   20% antistatic agent; and
   1% of one of the perfumery substances as set forth in Table II of Example VIII, supra.

Fabric softening compositions containing the substances as set forth in Table II of Example VIII, supra, essentially consist of a substrate having a weight of about 3 grams per 100 square inches; a substrate coating weighing about 1.85 grams per 100 square inches of substrate; and an outer coating weighing about 1.5 grams per 100 square inches of substrate are prepared, thereby providing a total aromatized substrate and outer coating weight ratio of about 1:1 by weight of the substrate.

The aromas as set forth in Table II of Example VIII, supra, are imparted in a pleasant manner to the headspace in a drier on operation thereof, using the said drier-added fabric softening, non-woven fabric by adding to the drying cycle.

As stated, supra, in the case of fabric softener articles, the entire U.S. Pat. No. 3,632,396 is incorporated by reference herein. Thus, all of the articles of U.S. Pat. No. 3,632,396, acting as fabric softening articles in said U.S. patent, may be perfumed in their outer coating with from 0.25% up to 5% by weight of each of the perfuming substances of Table II of Example VIII, supra.

EXAMPLE XVI

Hair Preparation

A "soft-feel, good-hold" hair spray is produced containing the following ingredients:

| Ingredients | Parts by Weight |
| --- | --- |
| Polyvinylpyrollidone/vinyl acetate "E-735 Copolymer" manufactured by the GAF Corporation of New York, NY | 4.00 |
| Anhydrous ethanol | 70.90 |
| Dioctyl sebecate | 0.05 |
| Benzyl alcohol | 0.05 |
| "Propellant A46" manufactured by the GAF Corporation of New York, NY | 24.95 |
| Fragrance ingredient as set forth in Table II of Example VIII, supra. | 0.05 |

The PVP/VA copolymers are first dissolved in alcohol and all other ingredients are added until uniform. The propellant is then pressurized and used as an aerosol. The resulting hair sprays each have pleasant aromas as set forth in Table II of Example VIII, supra.

EXAMPLE XVII

Scouring Cleanser Composition

A scouring cleanser composition is prepared in accordance with Example I at columns 11 and 12 of U.S. Pat. No. 4,193,888 issued on Mar. 18, 1980, the specification for which is incorporated by reference herein. To this composition, the substances as set forth in Table II of Example VIII, supra, are added at the level of 0.25% as set forth in the table in said Example I of U.S. Pat. No. 4,193,888, yielding an aroma on using said cleanser in ordinary circumstances which is quite pleasant and described in Table II of Example VIII, supra.

EXAMPLE XVIII

A fabric softening article prepared substantially as set forth in Example VII of Canadian Patent No. 1,069,260, the specification for which is incorporated by reference herein, is prepared containing 0.21% by weight of a perfuming substance as set forth in Table II of Example VIII, supra, and yielding on use in a drier, a faint aroma as set forth in Table II of Example VIII, supra.

EXAMPLE XIX

Pudding

At the rate of 0.8 ppm (i) the lactone produced according to Example I and (ii) the lactone produced according to Example VI are separately added to a ROYAL® Butterscotch Pudding.

When the lactone of Example I is added, pleasant, aesthetically pleasing, pear, plum-like, buttery and peach nuances were added to the butterscotch pudding with the panel of 30 members preferring the butterscotch pudding without the lactone of Example I added thereto.

When the lactone of Example VI is added, pleasant, aesthetically pleasing, peach, coconut and creamy nuances were added to the butterscotch pudding with the panel of 30 members preferring the butterscotch pudding with the lactone of Example VI added thereto to a butterscotch pudding without the lactone added thereo.

EXAMPLE XX

Flavor Formulations

The following natural rich orange formulations are prepared:

| Ingredients | Parts by Weight XX (A) | Parts by Weight XX (B) |
|---|---|---|
| The compound defined according to the structure: | 26.0 | 26.0 |
| prepared according to Example VI of U.S. Pat. No. 4,532,364. | | |
| The lactone produced according to Example I. | 12.00 | 0 |
| The lactone produced according to Example VI. | 0 | 12.0 |
| Natural lemon oil terpeneless | 10.0 | 10.0 |
| Acetaldehyde | 0.6 | 0.6 |
| α-Terpineol | 2.1 | 2.1 |
| Citral | 1.8 | 1.8 |
| Carvone | 0.24 | 0.24 |
| Terpinolene | 1.2 | 1.2 |
| α-Terpinene | 0.25 | 0.25 |
| Diphenyl | 0.25 | 0.25 |
| α-Fenchyl alcohol | 0.25 | 0.25 |
| Linalool | 0.25 | 0.25 |
| Limonene | 0.35 | 0.35 |
| Gereanyl acetate | 0.25 | 0.25 |
| Nootkatone | 0.25 | 0.25 |
| Neryl acetate | 0.25 | 0.25 |

A third flavor formulation is prepared which is identical to the above formulation, except without the lactones of Example I or Example VI.

The flavor formulation of Example 20A with the lactone of Example I has a definite, natural, rich orange aroma and taste with pear, plum-like, peach and butter nuances due to the addition of the pear, plum-like, peach and buttery principals to this citrus flavor.

The flavor formulation of Example XX(B) with the lactone of Example VI has a definite, rich orange aroma and taste with peach, coconut and creamy nuances due to the addition of peach, coconut and creamy principals to this citrus flavor.

The lactones of Examples I and VI added thereto are used in the following examples.

EXAMPLE XXI

(A) Powder Flavor Compositions

20 Grams of the flavor compositions of Examples XX(A) and XX(B) containing the lactones of Examples I and VI are emulsified in a solution containing 300 grams gum acacia and 700 grams water. The emulsions are spray-dried with a Bowen Lab Model Drier utilizing 260 c.f.m. of air with an inlet temperature of 500° F., an outlet temperature of 200° F. and a wheel speed of 50,000 rpm.

(B) Sustained Release Flavor

| Ingredients | Parts by Weight |
|---|---|
| Liquid citrus flavor compositions of Examples XX(A) and XX(B) (separately) | 20.0 |
| Propylene glycol | 9.0 |
| CAB-O-SIL ® M-5 (brand of silica produced by the Cabot Corporation of 124 High Street, Boston, MA 02109: Physical Properties: Surface area: 200 m$_2$/gm; Normal particle size: 0.012 microns; and Density: 2.3 lbs/cu. ft.) | 5.00 |

The CAB-O-SIL® M-5 is dispersed in the liquid citrus flavor compositions of Examples 20(A) and (20B) with vigorous stirring, thereby resulting in each case in a viscous liquid. 71 Parts by weight of the powder flavor compositions of Part (A), supra, are then separately blended into the said viscous liquids, with stirring, at 25° C. for a period of 30 minutes, resulting in a dry, free flowing, sustained release flavor powder.

EXAMPLE XXII

10 Parts by weight of 50 Bloom pigskin gelatin is added to 90 parts by weight of water at a temperature of 150° F. The mixture is agitated until the gelatin is completely dissolved and the solution is cooled to 120° F. Separately, 20 parts by weight of the liquid flavor compositions of Examples XX(A) and XX(B) are added to the solution, which is then homogenized to form an emulsion having particle size typically in the range of 5–40 microns. This material is kept at 120° F., under which conditions the gelatin will not jell.

Coacervation is induced by adding, slowly and uniformly, 40 parts by weight of a 20% aqueous solution of sodium sulfate. During coacervation, the gelatin molecules are deposited uniformly about each oil droplet as a nucleus.

Gelation is effected by pouring the heated coacervate mixtures into 1,000 parts by weight (each) of 7% aqueous solutions of sodium sulfate at 65° C. The resulting jelled coacervates may be filtered and washed with water at temperatures below the melting point of gelatin to remove the salt.

Hardening of the filtered cake, in this example, is effected by washing with 200 parts by weight of 37% solution of formaldehyde in water. The cake is then washed to remove residual formaldehyde.

EXAMPLE XXIII

Chewing Gum

100 Parts by weight of chicle are mixed with 4 parts by weight of each of the two flavors prepared in accordance with Example XXI(B). 300 Parts of sucrose and 100 parts of corn syrup are added. Mixing is effected in a ribbon blender with jacketed side walls of the type manufactured by the Baker Perkins Company.

The resulting chewing gum blends are then each manufactured into strips 1 inch in width and 0.1 inches in thickness. The strips are cut into lengths of 3 inches each. On chewing, each of the chewing gum has a pleasant, long-lasting, rich citrus flavor.

EXAMPLE XXIV

Toothpaste Formulation

The following separate groups of ingredients are prepared:

| Ingredients | Parts by Weight |
|---|---|
| Group A | |
| Glycerine | 30.200 |
| Distilled water | 15.325 |
| Sodium benzoate | 0.100 |
| Saccharin sodium | 0.125 |
| Stannous fluoride | 0.400 |
| Group B | |
| Calcium carbonate | 12.500 |
| Dicalcium phosphate (dihydrate) | 37.200 |
| Group C | |
| Sodium n-lauroyl sarcosinate (foaming agent) | 2.000 |
| Group D | |
| Flavor materials of Example 21B | 1.200 |

1. The ingredients in Group A are stirred and heated in a steam-jacketed kettle to 160° F.;
2. Stirring is continued for an additional 3 to 5 minutes to form a homogeneous gel;
3. The powders of Group B are added to the gel, while mixing, until a homogeneous paste is formed;
4. With stirring, one of the flavors Group D is added and, lastly, the sodium n-lauroyl sarcosinate; and
5. The resultant slurry is then blended for 1 hour. The completed paste is then transferred to a three-roller mill and then homogenized and, finally, tubed.

The resulting toothpastes, when used in normal toothbrushing procedures, yield pleasant, rich citrus flavors of constant, strong intensity throughout said procedure (1–1.5 minutes).

EXAMPLE XXV

Chewable Vitamin Tablets

The flavor materials produced according to the process of Example 21B are each added to a chewable vitamin tablet formulation at a rate of 10 grams/kilograms, which chewable vitamin tablet formulation is prepared as follows:

In a Hobart Mixer, the following materials are blended to homogenity:

| Ingredients | Grams/1,000 Tablets |
|---|---|
| Vitamin C (ascorbic acid) as ascorbic acid-sodium ascorbate mixture 1:1 | 70.0 |
| Vitamin $B_1$ (thiamine mononitrate) as ROCOAT ® thiamine mononitrate 33 ⅓ (Hoffman La Roche) | 4.0 |
| Vitamin $B_2$ (riboflavin) as ROCOAT ® riboflavin 33 ⅓ (Hoffman La Roche) | 5.0 |
| Vitamin $B_6$ (pyridoxine hydrochloride) as ROCOAT ® pyridoxine hydrochloride 33 ⅓ (Hoffman La Roche) | 4.0 |
| Niacinamide as ROCOAT ® niaacinamide 33 ⅓ (Hoffman La Roche) | 33.0 |
| Calcium pantothenate | 11.5 |
| Vitamin $B_{12}$ (cyanocobalamin) (Merck) 0.1% in gelatin | 3.5 |
| Vitamin E (dl-alpha tocopheryl acetate) as dry Vitamin E acetate 33 ⅓% (Hoffman La Roche) | 6.6 |
| d-Biotin | 0.004 |
| One of the flavors of Example XXI(B) | (as indicated above) |
| Certified lake color | 5.0 |
| Sweetener - sodium saccharin | 1.0 |
| Magnesium stearate lubricant | 10.0 |
| Mannitol | (q.s. to make) 500.0 |

Preliminary tablets are prepared by slugging with flat-faced punches and grinding the slugs to 14 mesh. 13.6 Grams of dry Vitamin A acetate and 0.6 grams of Vitamin D are then added as beadlets. The entire blend is then compressed using concave punches at 0.5 grams each.

Chewing of the resultant tablets yeilds pleasant, long-lasting, consistently strong, rich citrus flavors for a period of 12 minutes.

EXAMPLE XXVI

To 100 parts by weight of GOYA® Mango Nectar (produced by the Goya Corporation of New York, N.Y.) is added 10 ppm of the lactone produced according to Example I. The lactone mixture adds to the mango nectar a very natural nuance which, although present in natural mango (prior to adding the lactone of Example I), is lost in the canning process when the mango nectar is prepared and canned in the usual manner.

What is claimed is:

1. The δ-decalactone substantially having the structure:

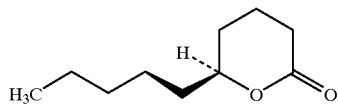

having an enantiomeric excess percent of 95.6 ([ϵϵ%=95.6]) with an optical rotation of +53.64° ([$\alpha_D^{20}$=+53.64°]).

2. A fragrance composition consisting essentially of a fragrance base and intimately admixed therewith an aroma augmenting, enhancing or imparting quantity and concentration of the compound defined according to claim 1.

3. A perfumed article consisting essentially of a perfumed article base and intimately admixed therewith an aroma augmenting, enhancing or imparting quantity and concentration of the compound defined according to claim 1.

4. A foodstuff composition consisting essentially of a foodstuff base and intimately admixed therewith a flavor augmenting, enhancing or imparting quantity and concentration of the compound defined according to claim 1.

5. A cologne composition comprising water, ethanol and an aroma augmenting, enhancing or imparting quantity and concentration of the compound defined according claim 1.

6. A process for augmenting, enhancing or imparting an aroma or taste in or to a consumable material selected from the group consisting of foodstuffs, fragrances, perfumed articles and chewing gums comprising the step of intimately admixing with a consumable material base, an aroma or taste augmenting, enhancing or imparting amount and concentration of the compound defined according to claim 1.

* * * * *